US011162073B2

(12) United States Patent
Shah et al.

(10) Patent No.: US 11,162,073 B2
(45) Date of Patent: Nov. 2, 2021

(54) METHODS FOR GENERATING FUNCTIONAL HEMATOPOIETIC STEM CELLS

(71) Applicants: The Brigham and Women's Hospital, Inc., Boston, MA (US); Children's Medical Center Corporation, Boston, MA (US)

(72) Inventors: Dhvanit I. Shah, Malden, MA (US); George Q. Daley, Weston, MA (US)

(73) Assignees: The Brigham and Women's Hospital, Inc., Boston, MA (US); Children's Medical Center Corporation, Boston, MA (US)

( * ) Notice: Subject to any disclaimer, the term of this patent is extended or adjusted under 35 U.S.C. 154(b) by 255 days.

(21) Appl. No.: 15/781,034

(22) PCT Filed: Dec. 2, 2016

(86) PCT No.: PCT/US2016/064706
§ 371 (c)(1),
(2) Date: Jun. 1, 2018

(87) PCT Pub. No.: WO2017/096215
PCT Pub. Date: Jun. 8, 2017

(65) Prior Publication Data
US 2019/0177695 A1 Jun. 13, 2019

Related U.S. Application Data

(60) Provisional application No. 62/332,853, filed on May 6, 2016, provisional application No. 62/262,464, filed on Dec. 3, 2015.

(51) Int. Cl.
*C12N 5/02* (2006.01)
*C12N 5/071* (2010.01)
*C12N 5/0789* (2010.01)
*A61K 35/28* (2015.01)
*A01K 67/027* (2006.01)

(52) U.S. Cl.
CPC ........ *C12N 5/0647* (2013.01); *A01K 67/0271* (2013.01); *A61K 35/28* (2013.01); *A01K 2207/12* (2013.01); *C12N 2501/999* (2013.01); *C12N 2506/00* (2013.01); *C12N 2506/28* (2013.01); *C12N 2506/45* (2013.01); *C12N 2533/52* (2013.01)

(58) Field of Classification Search
CPC .............. C12N 5/0647; C12N 2506/00; C12N 2506/28; C12N 2506/45
USPC ............................................... 435/372, 377
See application file for complete search history.

(56) References Cited

U.S. PATENT DOCUMENTS

2013/0171110 A1  7/2013  Woods et al.
2015/0238532 A1  8/2015  Frenette et al.

FOREIGN PATENT DOCUMENTS

| CN | 101213206 | 7/2008 |
| JP | 2012050357 A | 3/2012 |
| WO | WO 2013/116307 | 8/2013 |
| WO | WO 2014/113415 | 7/2014 |

OTHER PUBLICATIONS

Li et al., May 20, 2015, Methods in Molecular Biology, 1212: 183-193.*
Descamps et al., "Vascular differentiation from embryonic stem cells: Novel technologies and therapeutic promises," Vascular Pharmacology, May 2012, 56(5-6):267-279.
EP Extended European Search Report in European Application No. 16871607.4, dated Jul. 3, 2019, 7 pages.
International Preliminary Report on Patentability in International Application No. PCT/US2016/064706, dated Jun. 5, 2018.
Marks-Bluth et al, "Cell signaling pathways that mediate haematopoietic stem cell specification," International Journal of Biochemistiy and Cell Biology, Dec. 2012, 44(12):2175-2184.
Lee et al, "Biomechanical force in blood development: extrinsic physical cues drive pro-hematopoietic signaling," Differentiation, Jul. 2013, 86(3):92-103.
Li et al, "Application of fluid mechanical force to embryonic sources of hemogenic endothelium and hematopoietic stem cells," Methods Mol Biol., May 20, 2015, 1212:183-193.
SG Search Report in Singapore Appln. No. 11201804641W, dated Aug. 5, 2019, 8 pages.
Slukvin et al., "Hematopoietic specification from human pluripotent stem cells: current advances and challenges toward de novo generation of hematopoietic stem cells," Blood, Oct. 2013, 122(25):4035-4046.
International Search Report and Written Opinion dated Mar. 31, 2017 in International Application No. PCT/US2016/064706, 24 pgs.
Choi et al., "Identification of the Hemogenic Endothelial Progenitor and Its Direct Precursor in Human Pluripotent Stem Cell Differentiation Cultures," Cell Rep. 2012, vol. 2(3), p. 553-567.

(Continued)

*Primary Examiner* — Shin Lin Chen
(74) *Attorney, Agent, or Firm* — Fish & Richardson P.C.

(57) ABSTRACT

Described in the present application are methods for preparing populations of hematopoietic stem cells (HSCs), e.g., autologous and/or allogenic HSCs, using mechanical stretching or Trpv4 agonisists, and methods of use of the HSCs in transplantation. In some embodiments, the methods include providing a population comprising hemogenic endothelial (HE) cells, and (i) contacting the HE cells with an amount of an agonist of transient receptor potential cation channel-subfamily vanilloid member 4 (Trpv4); and/or (ii) subjecting the cells to cyclic 2-dimensional stretching, for a time and under conditions sufficient to stimulating endothelial-to-HSC transition. Also provided herein are methods for treating subjects who have, bone marrow, metabolic, and immune diseases; the methods include administering to the subject a therapeutically effective amount of hematopoietic stem cells (HSCs) obtained by a method described herein.

3 Claims, 15 Drawing Sheets

(56) References Cited

OTHER PUBLICATIONS

Dragoni et al., "A functional transient receptor potential vanilloid 4 (TRPV4) channel is expressed in human endothelial progenitor cells," J Cell Physiol. Jan. 2015, vol. 230(1), p. 95-104.

Singh et al., "Fibronectin and stem cell differentiation—lessons from chondrogenesis," J Cell Sci. 2012, vol. 125(Pt 16), p. 3703-3712.

Muramatsu et al., "Functional Gene Screening System Identified TRPV4 as a Regulator of Chondrogenic Differentiation," J Biol Chem. 2007, vol. 282(44), p. 32158-67.

Delorme et al., "Specific Lineage-Priming of Bone Marrow Mesenchymal Stem Cells Provides the Molecular Framework for Their Plasticity," Stem Cells. 2009, vol. 27(5), p. 1142-51.

Riehl et al., "Mechanical Stretching for Tissue Engineering: Two-Dimensional and Three-Dimensional Constructs," Tissue Eng Part B Rev. 2012, vol. 18(4), p. 288-300.

EP Office Action by European Appln No. 16871607.4, dated Apr. 14, 2021, 5 pages.

Adamo et al., "Biomechanical forces promote embryonic haematopoiesis." Nature, Jun. 2009, 459(7250):1131-5.

Anderson et al.,. "Hematopoietic stem cells develop in the absence of endothelial cadherin 5 expression," Blood, The Journal of the American Society of Hematology, Dec. 24, 2015, 126(26):2811-20.

Ando et al., "Reaction of blood flow shear stress and endothelial cells," BME, Feb. 10, 1991, 5(2), 8-19, 12 pages.

AU Office Action in Australian Appln. No. 2016362508, dated Dec. 2, 2020, 7 pages.

JP Japanese Office Action in Japanese Appln. No. 2018-528663, dated Jan. 26, 2021, 8 pages (with English translation).

SG Invitation to Respond to Written Opinion in Singapore Appln. No. 11201804641W, dated Jun. 13, 2020, 7 pages.

Yokota et al., "Current Topics in Regulatory Mechanisms of Hematopoiesis," Journal of Kyoto Prefectural University of Medicine, 2010, 119(10):681-693 (with English abstract).

CN Office Action in Chinese Appln. No. 201680080976, dated Jul. 15, 2021, 15 pages (with English translation).

Xie et al., "Advance in biomechanical study of embryonic vascular system development," Hereditas. Sep. 2012, 34(9):1123, 29 pages (with English translation).

* cited by examiner

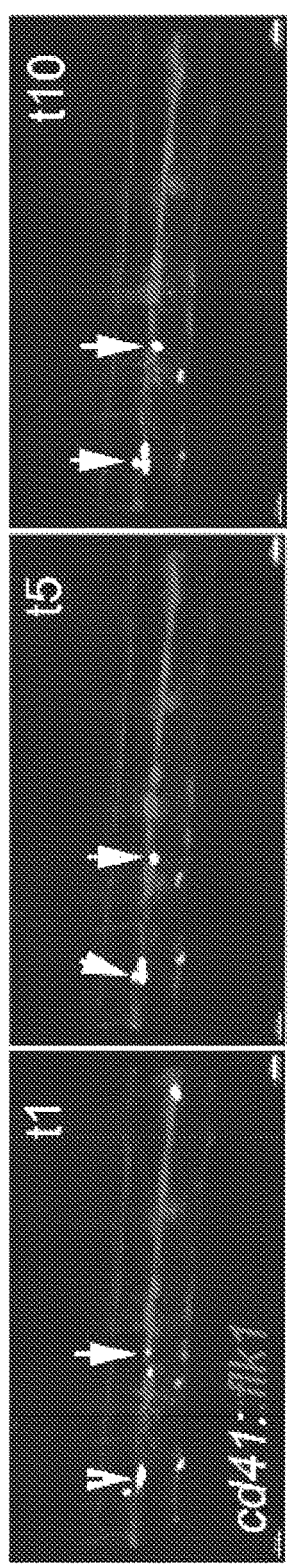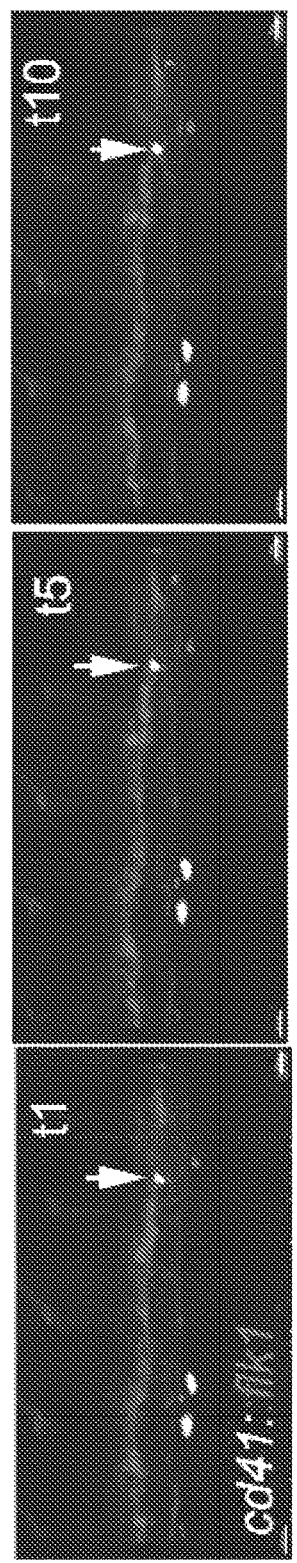
FIG. 1A wild-type
FIG. 1B cdh5-MO

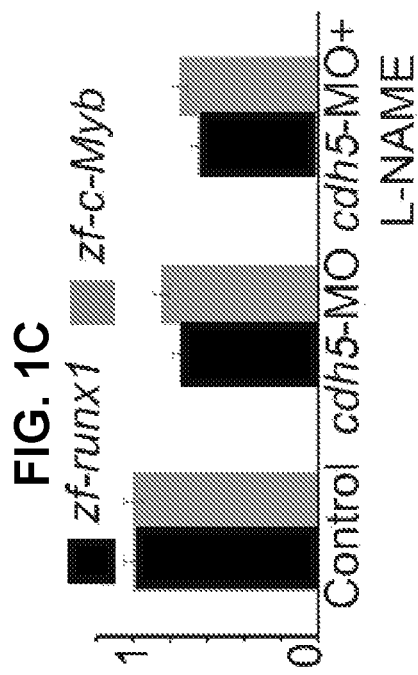
FIG. 1C
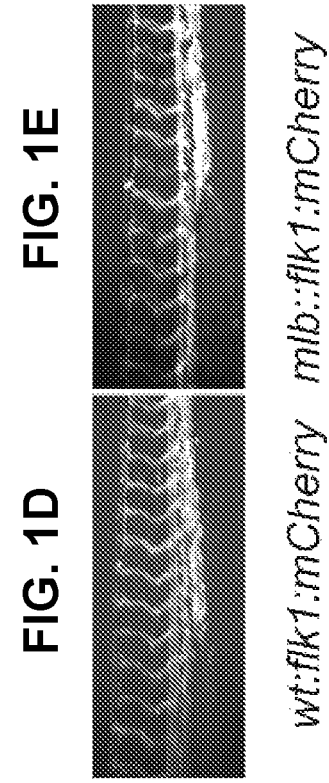
FIG. 1D
FIG. 1E

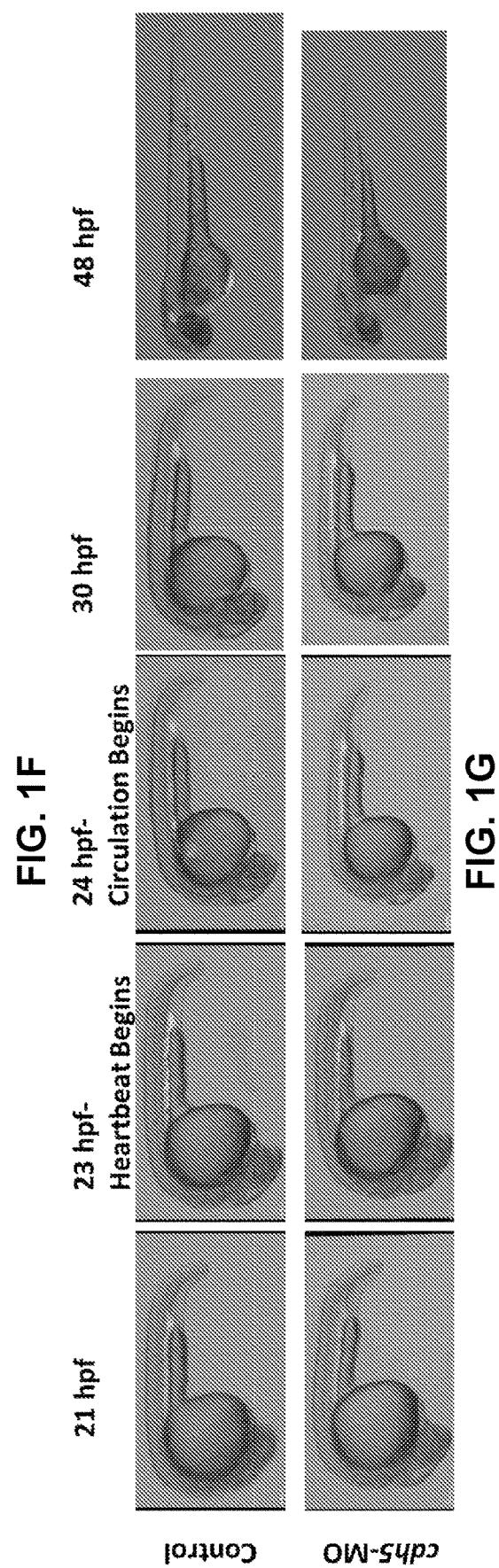

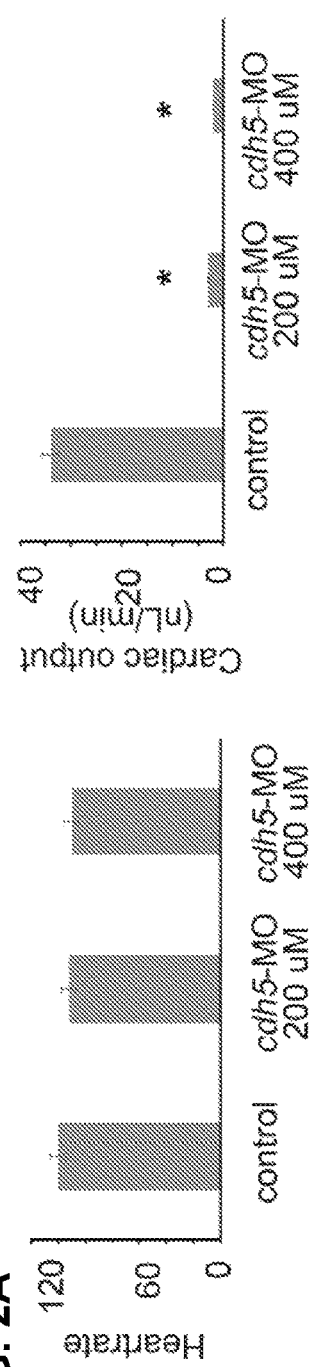
FIG. 2A
FIG. 2B
FIG. 2C

*cdh5*-MO; 48 hpf

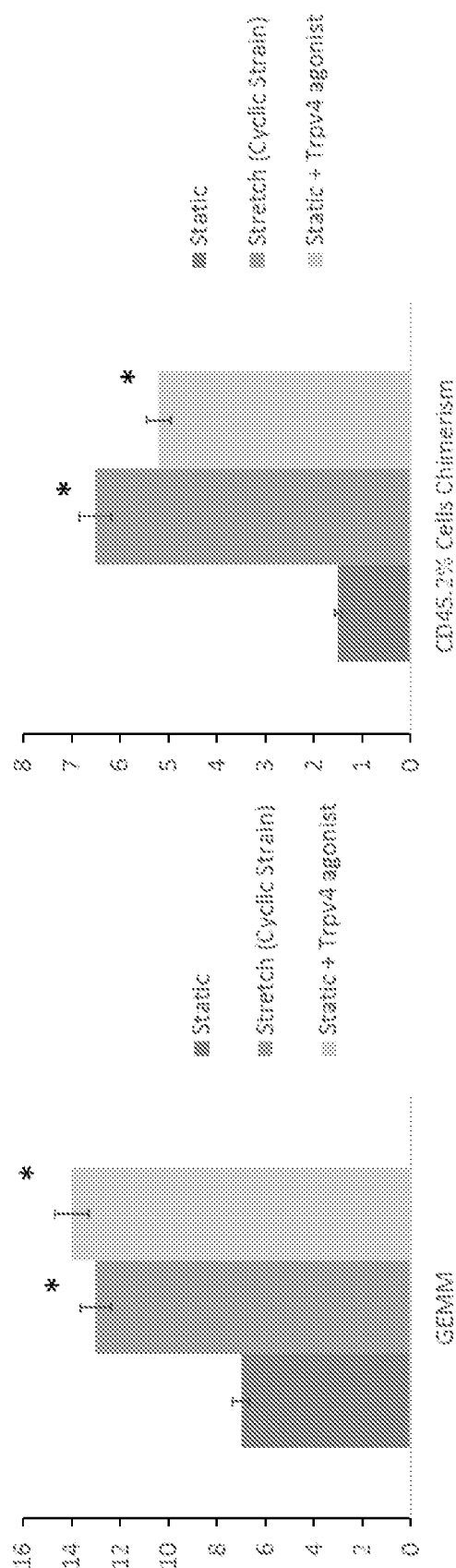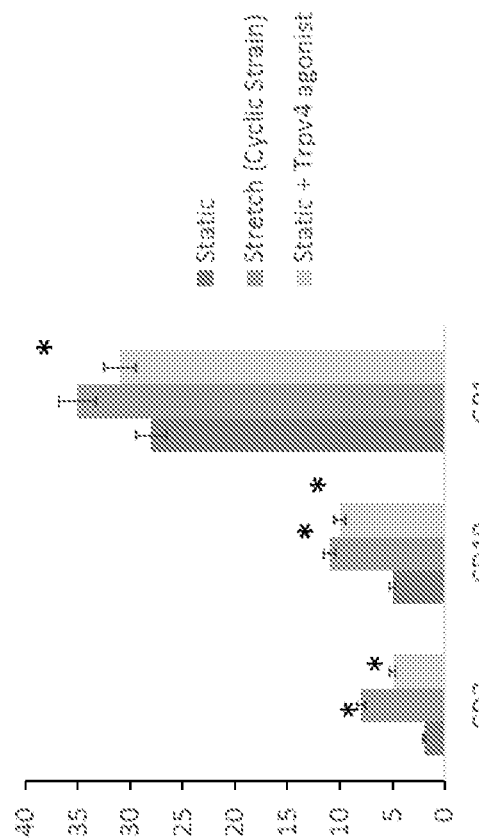
FIG. 5A
FIG. 5B
FIG. 5C

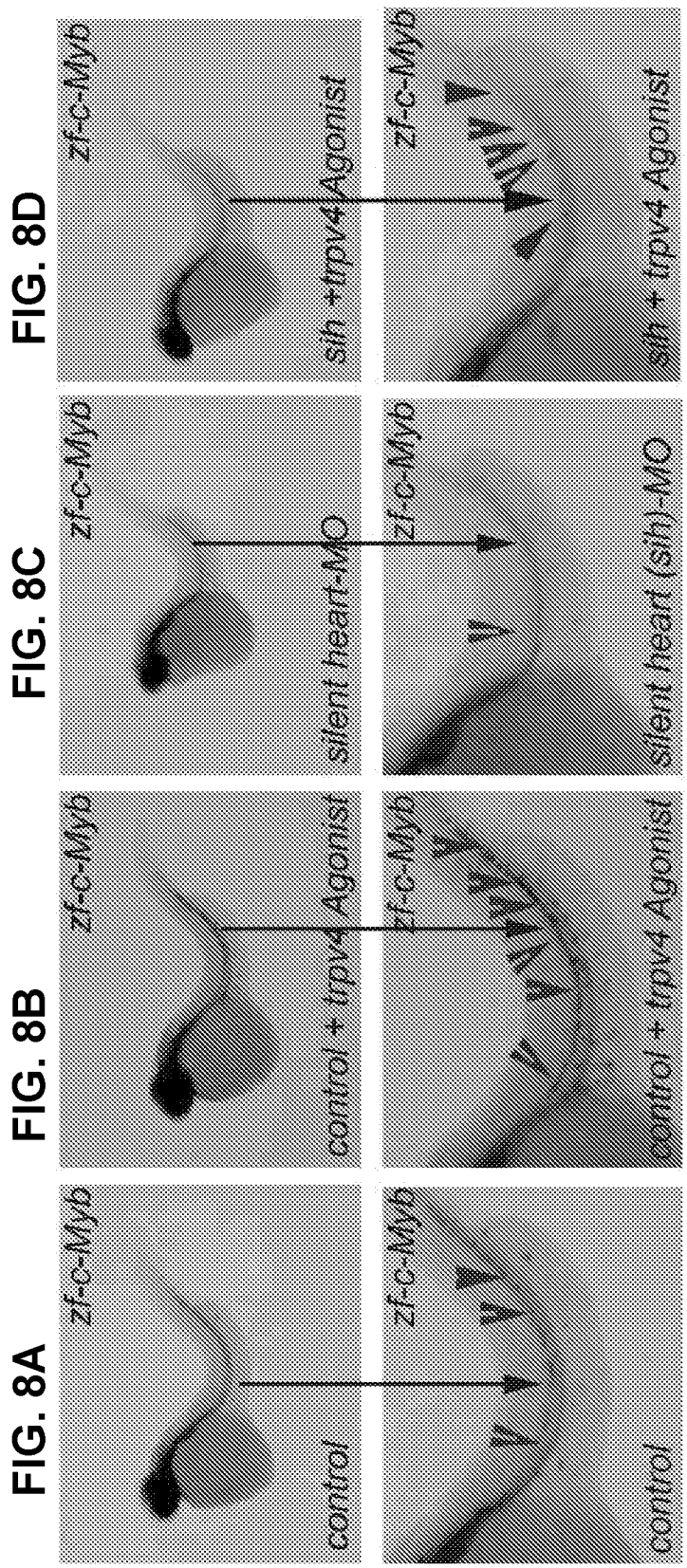

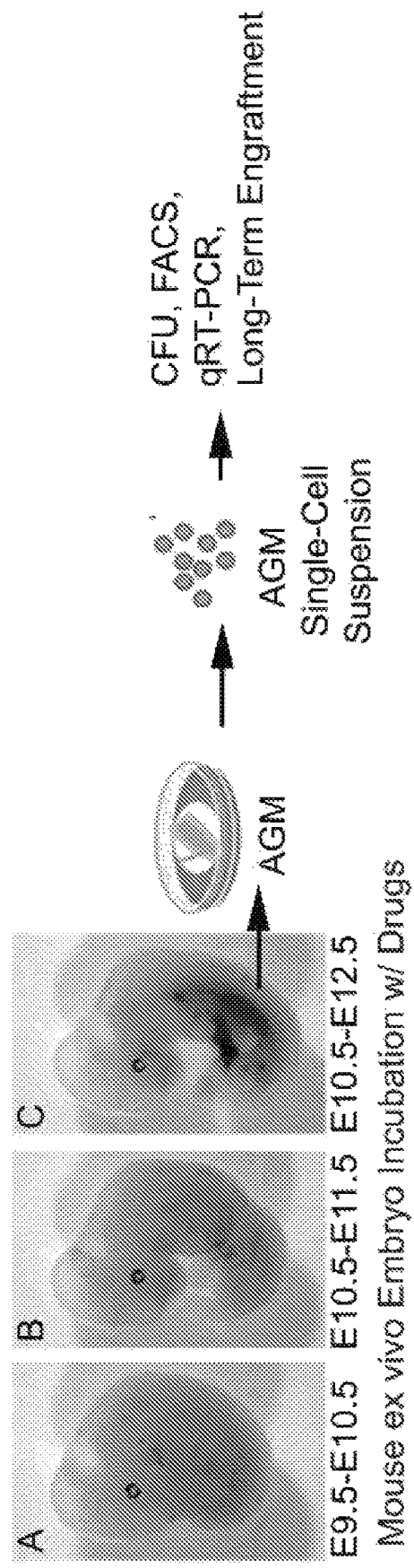

METHODS FOR GENERATING FUNCTIONAL HEMATOPOIETIC STEM CELLS

CLAIM OF PRIORITY

This application application is a § 371 National Stage Application of PCT/US2016/064706, filed Dec. 2, 2016, which claims the benefit of U.S. Provisional Application Ser. No. 62/262,464, filed on Dec. 3, 2015, and 62/332,853, filed on May 6, 2016. The entire contents of the foregoing are incorporated herein by reference.

FEDERALLY SPONSORED RESEARCH OR DEVELOPMENT

This invention was made with Government support under Grant No. 5K01DK085217, 2R03DK100672, and 5R01HL131645 awarded by the National Institutes of Health. The Government has certain rights in the invention.

TECHNICAL FIELD

Described herein are methods for preparing populations of hematopoietic stem cells (HSCs), e.g., autologous and/or allogenic HSCs, using mechanical stretching or Trpv4 agonisists, and methods of use of the HSCs in transplantation.

BACKGROUND

HSC transplantation (HSCT) is widely used to treat patients with blood, bone marrow, metabolic, and immune diseases (1-5). Despite advances in umbilical cord and haplo-identical stem cell transplantation, the therapeutic use of HSC transplantation is often restricted due to the difficulty of finding suitable human leukocyte antigen (HLA)-matched donors in a timely manner, especially in countries with ethnic minorities and lack of national unrelated donor registries (6-9). Although mixed-race persons account for 1.6 percent (9.7 million) of the U.S. population, multiracial volunteers make up only 3 percent (21,000) of the 7 million people on the registry, leaving 6,000 patients without a bone marrow match. Even if one finds a suitable match, immunologic complications such as graft-versus-host disease (GVHD), donor rejection, and high treatment-related mortality could compromise patient survival. However, these complications are eliminated by autologous transplant. Although autologous HSCs would not replace allogeneic HSCs entirely, especially in the context of hematologic malignancy, they would overcome major hurdles in HSCT including, lack of donor availability and GVHD for patients with a broad span of malignant and non-malignant hematologic, immune, and metabolic disorders (3-5, 15).

SUMMARY

Described herein are methods for developing human hemogenic endothelial cell derived, clinical-grade HSCs for treating malignant and non-malignant hematologic, metabolic, and immune disorders.

Thus, described herein methods for preparing populations of hematopoietic stem cells (HSC). The methods include providing a population comprising hemogenic endothelial (HE) cells, and (i) contacting the HE cells with an amount of an agonist of transient receptor potential cation channel-subfamily vanilloid member 4 (Trpv4); and/or (ii) subjecting the cells to cyclic 2-dimensional strectching, for a time and under conditions sufficient to stimulating endothelial-to-HSC transition.

In some embodiments, the subject does not have a hematological malignancy.

Also provided herein are methods for treating subjects who have, bone marrow, metabolic, and immune diseases; the methods include administering to the subject a therapeutically effective amount of hematopoietic stem cells (HSCs) obtained by a method described herein, e.g., a method comprising: providing a population comprising hemogenic endothelial (HE) cells, and (i) contacting the HE cells with an amount of an agonist of transient receptor potential cation channel-subfamily vanilloid member 4 (Trpv4); and/or (ii) subjecting the cells to cyclic 2-dimensional stretching, for a time and under conditions sufficient to stimulating endothelial-to-HSC transition.

In some embodiments, the HE cells used in the methods described herein are obtained from induced pluripotent stem cells (iPSC), e.g., skin or CD34+ cells are first converted to induced pluripotent stem cells (preferably human iPSCs) using established methods. Then such human iPSCs are differentiated into human HE cells using methods known in the art and/or described herein. For example, differentiation of human iPSCs into EBs can occur in presence of drugs, growth factors, cytokine cocktails to induce hemogenic endothelial fate, followed by sorting of cells between day 7-9 and further incubation with an established cocktail to enrich HE cells.

In some embodiments, the agonist of Trpv4 is selected from the group consisting of Arachidonic Acid, 5,6-EET, 8,9-EET, bisandrographolide A (BAA), Phorbol ester (e.g., 4α-PDD and 4α-PDH), RN-1747, substituted 1,4-diaminobutane or 1,3-diaminopropane analogues; and GSK10116790A.

In some embodiments, the HE cells or iPSC are obtained from a subject who has a blood, bone marrow, metabolic, or immune disease.

In some embodiments, the agonist of Trpv4 is selected from the group consisting of Arachidonic Acid, 5,6-EET, 8,9-EET, bisandrographolide A (BAA), Phorbol ester (e.g., 4α-PDD and 4α-PDH), RN-1747, substituted 1,4-diaminobutane or 1,3-diaminopropane analogues; and GSK10116790A.

In some embodiments, the subject is a mammal, e.g., a human.

In some embodiments, the subject has multiple myeloma; non-Hodgkin lymphoma; Hodgkin disease; acute myeloid leukemia; neuroblastoma; a germ cell tumor; an autoimmune disorder (systemic lupus erythematosus (SLE) or systemic sclerosis); or amyloidosis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-G Hematopoietic stem cells emerge despite inhibition of the shear-stress pathway and early circulation arrest. (A-B) Time-lapse confocal imaging of cd41:eGFP$^+$ HSCs emerging from flk1: mCherry$^+$ endothelial cells in the control and cdh5-silenced embryos between 30-42 hpf, suggesting that the loss of cdh5, and thus impaired circulation, does not affect the endothelial emergence of cd41: eGFP$^+$ HSCs (examples are marked with arrows). (C) qRT-PCR analyses of zf-runx1 and zf-c-Myb expression levels, demonstrating expression levels of HSC surrogate markers are normal despite the loss of cdh5 and inhibition of NOS pathway in cdh5-morphant embryos. (D-E) Confocal imaging of wild-type (control) flk1:mCherry and malbec::flk1: mCherry demonstrates that arteries and veins are formed in the absence of cdh5. (F-G) Time-lapse confocal imaging of lcr:eGFP$^+$ red cell as well as flk1:mCherry$^+$ vascular structure formation between 21-48 hpf. At 21 hpf, red cells from primitive hematopoiesis are present in the AGM region. As soon as the heartbeat begins at 23 hpf, red cells begin circulating in control embryos and expression of endothelial markers is visible between 25-48 hpf, which demonstrates vasculature formation. In contrast, lcr:eGFP$^+$ red cells are accumulated in the AGM region in the cdh5-morphants despite the beginning of a heartbeat and vascular formation, demonstrating early circulation arrest.

FIGS. 2A-E. cdh5-morphant embryos have normal heartrate, impaired cardiac output, and abnormal heart morphology. (A) Electrocardiography of the zebrafish heart in the control and cdh5-morphant embryos (0.2-0.4 mM), demonstrating that cdh5-morphants have a normal heartrate. (B) Cardiac output in the control and cdh5-morphant embryos (0.2-0.4 mM), demonstrating that the cdh5-morphants have no cardiac output. (C) Micro-angiography of the cdh5-morphant, demonstrating that fluorescent dye injected in the cdh5-morphant heart is entrapped in the atrium of the heart, as seen with pericardial edema. (D) Immunohistochemistry of hearts isolated from control and cdh5-morphant embryos using antibodies against cardiomyocyte myosin heavy chain (MF20) and endothelial cells (F1k1), suggesting that atrium, ventricle, and outflow tract are distorted. *P<0.05

FIGS. 5A-C. 2D circumferential stretch stimulates HSC formation. (A) Colony formation unit assay to measure multipotent GEMM colonies (marker of HSPCs) following 2D cyclic strain (6%, 24 h) and transient receptor potential cation channel-subfamily vanilloid member 4 (Trpv4) agonist (GSK10116790A, referred to herein as GSK101) treatment of E11.5 AGM cells. (B) Percentage of CD45.2$^+$ peripheral blood chimerism in static E11.5 AGM, 2D cyclic strain-treated E11.5 AGM, and Trpv4 agonist (GSK 101) treated AGM-transplanted recipients after 8 weeks. Each recipient was transplanted with 2 e.e. AGM. (C) Quantitative lineage analysis of peripheral blood from mice transplanted with static E11.5 AGM, 2D cyclic strain treated E11.5 AGM, and Trpv4 agonist (GSK 101)-treated E11.5 AGM after 8 weeks. Increase in GEMM, % CD45.2 peripheral blood chimerism, and % multi-lineage reconstitution demonstrated that 2D cyclic strain, and Trpv4 activation stimulate HSC formation in this customized organ-on-a-chip model. n=6; *P<0.05 vs static control.

FIGS. 8A-D. Activation of Trpv4 enhances HSPC formation in normal embryos and rescues HSC formation in silent heart (sih) embryos. Whole-mount in situ hybridization for HSPC marker (c-myb) expression demonstrates that the incubation of control embryos with Trpv4 agonist (GSK101) enhances HSPC formation (FIG. 8A vs 8B), whereas the incubation of silent heart (sih)-MO embryos with Trpv4 agonist (GSK101) rescues HSPC formation (FIG. 8A vs 8C vs 8D). n=120 in each group; examples of c-myb$^+$ HSPC clusters are denoted by arrows.

FIGS. 10A-D. Schematic representation of the ex vivo mouse embryo culture with stretch-activated ion channel modulators followed by analyses of their hematopoietic function. We have optimized conditions to culture mouse embryo(s) from E9.5 to E10.5 (A), E10.5 to E11.5 (B), and E10.5 to E12.5 (C) using our customized mouse embryo incubation unit. We verify the growth of embryos by counting the number of somites at each developmental stage and analyse hematopoietic function (D).

DETAILED DESCRIPTION

Figure 2D:
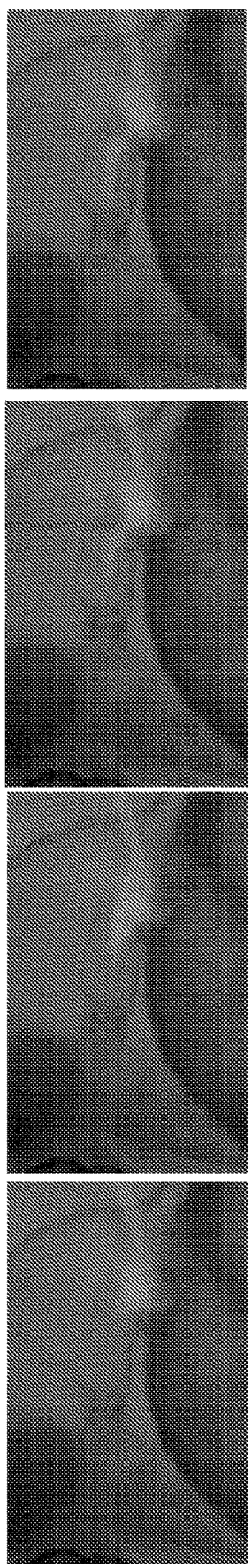

During fetal development, a subset of endothelial cells in the aorta-gonad-mesonephros (AGM), termed hemogenic endothelial cells, change their fate to become HSCs that ultimately colonize the fetal liver and bone marrow (10, 11). However, the identities of the factors stimulating hemogenic endothelial cells remain elusive, limiting the utility of hemogenic endothelial cells as a potential source of functional HSCs. Blood flow-mediated shear-stress on the endothelial lining is the only known biomechanical force stimulating the endothelial emergence of HSCs (12, 13). Using Cdh5-null zebrafish and murine models, it was recently established that functional HSCs emerge despite early circulation arrest (14). These cdh5-silenced models were used as a pivot to study shear-stress independent biomechanical forces triggering functional HSC emergence, to investigate additional mechanisms by which pulse-pressure-mediated circumferential stretch governs HSC emergence.

Attempts to generate HSCs from hemogenic endothelial cells in the laboratory have been largely unsuccessful, in part due to a lack of knowledge about factors that stimulate HSC emergence from hemogenic endothelial cells.

As described herein, micro-angiography, echocardiography, 3D digital Doppler ultrasound, and time-lapse confocal imaging established that circumferential vascular stretch due to pulsations from a beating heart triggers functional HSCs to emerge from hemogenic endothelial cells, which can ultimately engraft and differentiate into definitive lineages. In addition, the activation of stretch-sensitive transient receptor potential cation channel-subfamily vanilloid member 4 (Trpv4) channels rescued HSC formation in silent heart (tnnt2; sih)-silenced embryos in the absence of heartbeat and blood flow.

The present findings establish new ex vivo methods (employing 2D circumferential stretch) and novel pharmacological target(s) (Trpv4 and/or modulators of the immediate early response genes (IEGs, a class of transcriptional factors; CREB, c-Fos, Elk1, NFAT)) to stimulate functional HSC formation. The present methods allow for the establishment of hemogenic endothelial cells as a bone marrow-independent source of functional HSCs in the treatment of blood, bone marrow failure, metabolomics, and immune disorders.

The unbiased zebrafish genetic screen described herein investigated the origin and development of hematopoietic cells, and led to the identification of new cell-extrinsic and -intrinsic factors that could stimulate the endothelial transition to HSCs in zebrafish, mouse, and human. Blood flow- and shear-stress-mediated activation of NOS have been implicated as a trigger for HSC emergence from the hemogenic endothelium during fetal development (12, 13). Under this model, one might predict that the absence of blood flow would compromise hematopoietic cell formation. Using zebrafish and mouse models, it however was established that functional HSCs emerge in the absence of blood flow (14). To analyze novel biomechanical forces stimulating the endothelial-to-HSC transition, the present experiments illustrated that pulse-pressure-mediated circumferential stretch stimulated functional HSC formation via the activation of Trpv4 signaling, and establish circumferential stretch as a novel biomechanical force and Trpv4 as a novel molecular mechanism stimulating the endothelial emergence of HSCs. Thus, the present methods provide a platform to use hemogenic endothelial cells as a new and safe source of functional HSCs in the treatment of human blood, immune, metabolic, and bone-marrow failure diseases.

The present disclosure describes how the hemogenic endothelium transitions to HSCs during fetal development, and provides methods to recapitulate this process, at least in part. As demonstrated herein, HSCs emerge, migrate, self-renew, engraft, and differentiate despite impaired blood circulation and/or NOS inhibition. Therefore, blood flow- and shear stress-independent, cell-extrinsic mechanisms regulating endothelial emergence and development of HSCs must exist. Micro-angiography, confocal imaging, 3D Doppler ultrasound, gene-expression analyses, and echocardiography data demonstrated that pulse-pressure-mediated circumferential stretch stimulates the endothelial transition to HSCs. An organ-on-a-chip was used to recapitulate in situ circumferential stretch conditions on mouse E11.5 AGM and/or AGM-derived endothelial, hemogenic endothelial, hematopoietic, vascular, and mesenchymal stromal cells. The circumferential stretch activates Trpv4 ion channels, which are expressed on endothelial and hematopoietic tissues. In addition, Trpv4 activation increases HSC formation and rescues hematopoiesis in silent heart-silenced embryos. The identification of circumferential stretch as a new biomechanical, cell-extrinsic factor stimulating HSC emergence will model the hemogenic endothelium as a potential source of functional HSCs.

Hemogenic Endothelial Cells

The present methods include the use of hemogenic endothelial cells to generate HSC. The hemogenic endothelial cells (e.g., Flk1+ CD45+ cells, Flk1+CD41+ cells or CD31+CD43+ cells) can be obtained in any manner, including from an allogeneic donor or from the subject to be treated with the HSC (i.e., autologous hemogenic endothelial cells, e.g., generated from iPSC created using cells from the recipient). Methods for isolating hemogenic endothelial cells are known in the art, and include generation from human pluripotent stem cells. See, e.g., Example 3 herein and Ditadi et al., Nature Cell Biol. 17(5) 580-591 (2015); Nakajima-Takagi et al., Blood. 2013;121(3):447-458; Zambidis et al., Blood. 2008 Nov. 1; 112(9):3601-14 and Park et al., Cytometry A. 2013 January; 83(1): 114-126 (human embryoid body (hEB)-based hemato-endothelial differentiation methods for efficient hiPSC differentiation); Choi et al., Cell Rep. 2012 Sep. 27; 2(3): 553-567. (hPSC differentiation in coculture with OP9); Sandler et al., 2014 Jul. 17; 511 (17509):312-318 (endothelial cells to hematopoietic cells); see also Sluvkin, Blood 2013 122:4035-4046.

Generating HSC from Hemogenic Endothelial (HE) Cells

The present methods can be used to generate HSC from HE cells in vitro, and can include incubating the cells in the presence of Trpv4 agonists and/or subjecting the cells to stretch, e.g., to cyclic stretching.

Trpv4 Agonists

Trpv4 is a member of the TRPV subfamily of Transient Receptor Potential (TRP) ion channels. The channel can be activated by physical stimuli (e.g., cell swelling or stretch and innocuous warming, e.g., to about 27-35° C.) and by chemical ligands including Arachidonic Acid and 5,6-EET and 8,9-EET (Watanabe et al., Nature 424:434-438 (2003), (Vincent and Duncton, Current topics in medicinal chemistry 11(17):2216-26 (2011)); bisandrographolide A (BAA, Smith et al., J Biol Chem 281:29897-29904 (2006)); Phorbol esters such as 4α-PDD and 4α-PDH (Watanabe et al., J Biol Chem 277:13569-13577 (2002); Vincent and Duncton, Current topics in medicinal chemistry 11(17):2216-26 (2011)); RN-1747; substituted 1,4-diaminobutane or 1,3-diaminopropane analogues (Vincent and Duncton, Current topics in medicinal chemistry 11(17):2216-26 (2011)); and GSK10116790A (Thorneloe et al., J Pharmacol Exp Ther 326:432-442 (2008)). See, e.g., compounds disclosed in Vriens et al., Mol Pharmacol 75 (6)1262-1279 (2009); Vriens et al., Curr Neuropharmacol. 6(1): 79-96 (2008); Vincent and Duncton, Current topics in medicinal chemistry 11(17):2216-26 (2011); WO2007098393; WO2007030761; WO2006105475; WO2007070865; WO2007082262; WO2007082262; and Jeong et al., In 238th ACS National Meeting, Washington, DC, United States, Aug. 16-20, 2009; Washington, DC, United States, 2009; MEDI-392.

Stretch

Alternatively or in addition, mechanical means can be used to apply stretching forces to the cells. For example, a computer controlled vacuum pump system (e.g., the Flex-Cell™ Tension System) attached to a nylon-membrane of a flexible-bottomed culture plate can be used to apply 2D circumferential stretch ex vivo to HE-derived cells under defined and controlled cyclic strain conditions, e.g., as described herein.

Methods of Use

The methods described herein can be used to generate populations of HSC for use in transplantation protocols, e.g., to treat blood (malignant and non-malignant), bone marrow, metabolic, and immune diseases. In some embodiments, the HSC are derived from autologous cells, e.g., generated from iPSC created using cells from the recipient subject. In some embodiments, e.g., wherein autologous-derived cells are used, the recipient subject has a condition selected from multiple myeloma; non-Hodgkin lymphoma; Hodgkin disease; acute myeloid leukemia; neuroblastoma; Germ cell tumors; autoimmune disorders (systemic lupus erythematosus (SLE), systemic sclerosis); amyloidosis; or other condition treatable using an autologous HSC transplant. In some embodiments wherein autologous-derived cells (e.g., wherein the HSC are generated from cells from the recipient subject) are used, the recipient subject does not have a hematological malignancy. In some embodiments, the recipient subject has Acute myeloid leukemia; Acute lymphoblastic leukemia; Chronic myeloid leukemia; Chronic lymphocytic leukemia; Myeloproliferative disorders; Myelodysplastic syndromes; Multiple myeloma; Non-Hodgkin lymphoma; Hodgkin disease; Aplastic anemia; Pure red-cell aplasia; Paroxysmal nocturnal hemoglobinuria; Fanconi anemia; Thalassemia major; Sickle cell anemia; Severe combined immunodeficiency (SCID); Wiskott-Aldrich syndrome; Hemophagocytic lymphohistiocytosis; Inborn errors of metabolism; Epidermolysis bullosa; Severe congenital neutropenia; Shwachman-Diamond syndrome; Diamond-Blackfan anemia; or Leukocyte adhesion deficiency; in these embodiments, preferably allogeneic-derived cells (e.g., HSC generated from cells from a subject other than the recipient subject, e.g., a subject who is matched with the recipient subject based on blood type and Human leukocyte antigen (HLA) typing) are used.

The methods can include administering the HSC generated using a methods described herein to a subject, e.g., by intravenous infusion or intrabone marrow transplantation. The methods can be performed following myeloablative, nonmyeloablative, or immunotoxin-based (e.g. anti-c-Kit, etc.) conditioning regimes.

EXAMPLES

The invention is further described in the following examples, which do not limit the scope of the invention described in the claims.

Example 1

Analysis of the Cellular Physiology of the Effects of Circumferential Stretch on the Endothelial Emergence of HSCs Introduction During embryonic development, blood flow generates shear stress on the ventral wall of the aortic endothelial lining and stimulates the endothelial transition to HSCs (12). Shear stress further activates the endothelial NOS pathway, which triggers the endothelial emergence of HSCs (13). It was recently demonstrated that functional HSCs emerge, develop, engraft, and reconstitute multi-lineage adult blood in the absence of active blood-circulation (14). Therefore, this example investigated new cell-extrinsic mechanisms stimulating the endothelial emergence of HSCs. Using 3D Doppler ultrasound, micro-angiography, echocardiography, and confocal imaging, we demonstrated that pulse-pressure generates circumferential stretch on blood vessels (FIGS. 1-3). We developed AGM-on-a-chip to recapitulate circumferential stretch conditions ex vivo by applying cyclic strain on a single-cell suspension of E11.5 AGM-hemogenic endothelial cells overlaid on a flexible nylon membrane of the FlexCell well (FIG. 4). We found that 2D circumferential stretch on E11.5 AGM cells stimulated HSC formation (FIG. 5).

Research Design

In mice, HSCs begin to emerge from AGM-hemogenic endothelial cells between E10.5 and E12.5. These HSCs colonize the fetal liver between E12.5 and E15.5, and ultimately engraft in the bone marrow and reconstitute multi-lineage blood (10, 21-26). We harvested E10.5 or 11.5 embryos from time-mated pregnant mice, dissected the AGM, and made a single-cell suspension to sort endothelial, hemogenic endothelial, hematopoietic, vascular, and/or mesenchymal stromal cells.

To recapitulate in situ circumferential stretch conditions using AGM-derived cells, we used the FlexCell FX-5000 Tension System based organ-in-a-dish (a.k.a. organ-on-a-chip or bioreactor) approach. Our computer-regulated, vacuum pressure based bioreactor generates 2D circumferential stretch ex vivo on AGM-derived cells by applying defined and controlled cyclic strain conditions on cells growing on the nylon-membrane of a flexible-bottomed culture plate (FIG. 4).

We first coated each well of the 6-well FlexCell plate using Fibronectin/Matrigel and allowed it to settle on the nylon membrane of each well. Then we seeded two embryo equivalent (e.e.) single-cell suspension of AGM (composed of endothelial, hemogenic endothelial, hematopoietic, vascular smooth muscle (VSMCs), and mesenchymal stromal cells)-derived cells in each FlexCell well, with a coating of Fibronectin/Matrigel allows AGM-derived (sorted or not sorted) cells to adhere to the bottom of the well. We filled each well with an explant culture medium containing Myelocult and growth factors (27, 28). We put these 6-well plates into the FlexCell machine and applied cyclic strain (4-12%) for 6-48 hours using customized pins hooked to the bottom of each well. We inserted the customized rubber gasket in several wells to simulate static control conditions as well. Next we added drugs modulating the stretch-activated ion channel signaling in a few wells undergoing the external cyclic strain. After 6-48 hours of external stimulation of circumferential stretch, we harvested AGM-derived cells from the FlexCell plate and analyzed their capacity to make hematopoietic cells: (I) We performed CFU assays using Methocult media to count multi-potential granulocyte, erythroid, macrophage, megakaryocyte progenitors (GEMM), granulocyte-macrophage progenitors (CFU-GM, CFU-M, CFU-G), and erythroid progenitor (BFU-E) colonies after seven days of seeding AGM derived sorted cells. (II) We analyzed the expression levels of Runx1, c-Myb, Lmo2, Gata2, CD144, and Gata1. (III) We also stained AGM-derived cells with fluorescently labeled conjugated antibodies to measure the expression levels of Flk1, CD144, CD41, c-Kit, & CD45.2. (IV) We injected two e.e. AGM (donor; CD45.2)-derived cells in sub-lethally irradiated CD45.1 (SJL; recipient) mice. We analyzed long-term engraftment and multi-lineage reconstitution potential of donor cells for 16 weeks followed by serial-transplantation to differentiate between HSCs and hemogenic endothelial cells. (V) We also performed limiting dilution assays to analyze the number of HSCs generated per AGM-derived cell following 2D circumferential stretch.

Results

An unbiased zebrafish chemical mutagenesis screen yielded malbec, a mutant for vascular endothelial cadherin (ve-cdh, cdh5). Cdh5 is a cell-adhesion molecule that helps preserve endothelial permeability and the integrity of the endothelial lining (16-18). The loss of cdh5 resulted in no cardiac output and impaired active blood circulation. malbec, cdh5-morphant embryos, Cdh5$^{-/-}$Gfp$^+$:Cdh5$^{+/+}$Gfp$^-$ chimera, and Cdh5$^{fl/fl}$:Scl-Cre-ERT mouse embryos had normal primitive and definitive hematopoiesis despite early circulation arrest (14).

In zebrafish the heart begins to beat around 23 hpf, the blood circulation begins at approximately 24-26 hpf, and definitive HSCs emerge from hemogenic endothelial cells in the AGM region between 26-48 hpf (11). Blood flow generates shear-stress on the ventral wall of the aortic endothelium and stimulates the endothelial-to-HSC transition by activating the NOS pathway (12, 13). When we performed time-lapse confocal imaging of both the control and the cdh5-silenced cd41:eGFP:flk1:mCherry embryos between 30-48 hpf, we found cdh5-silenced cd41:eGFP$^{low}$ HSCs emerging from flk1:mCherry$^+$ endothelial cells despite early circulation arrest (FIG. 1A-B). In addition, we incubated cdh5-silenced embryos in the presence of L-NAME, a pharmacological inhibitor of NOS (12), between 19-48 hpf. We found that NOS inhibition did not abolish HSC formation in the cdh5-silenced embryos (FIG. 1C). Thus, HSCs would emerge from hemogenic endothelial cells, despite impaired circulation and NOS inhibition. These striking data led us to investigate shear stress-independent biomechanical and molecular mechanisms responsible for the endothelial transition to HSCs.

To document whether circulation is impaired in the cdh5-silenced embryos, we analyzed the vascular structure and blood circulation in the cdh5-silenced embryos. We first performed confocal imaging of blood vessels in the control and in the cdh5-silenced flk1:mCherry embryos. We found that both arteries and veins were intact in cdh5-silenced embryos (FIG. 1D-E). Next, we analyzed the circulation of red blood cells in blood vessels before and after the heart begins to beat using time-lapse confocal imaging of the control and cdh5-silenced lcr:eGFP::flk1:mCherry embryos. We found that lcr: eGFP$^+$ red cells were accumulated in blood vessels of cdh5-silenced embryos even after the heart begins to beat (FIG. 1F-G). These data demonstrate that cdh5-morphants did not have active circulation despite the formation of blood vessels.

Figure 2E:
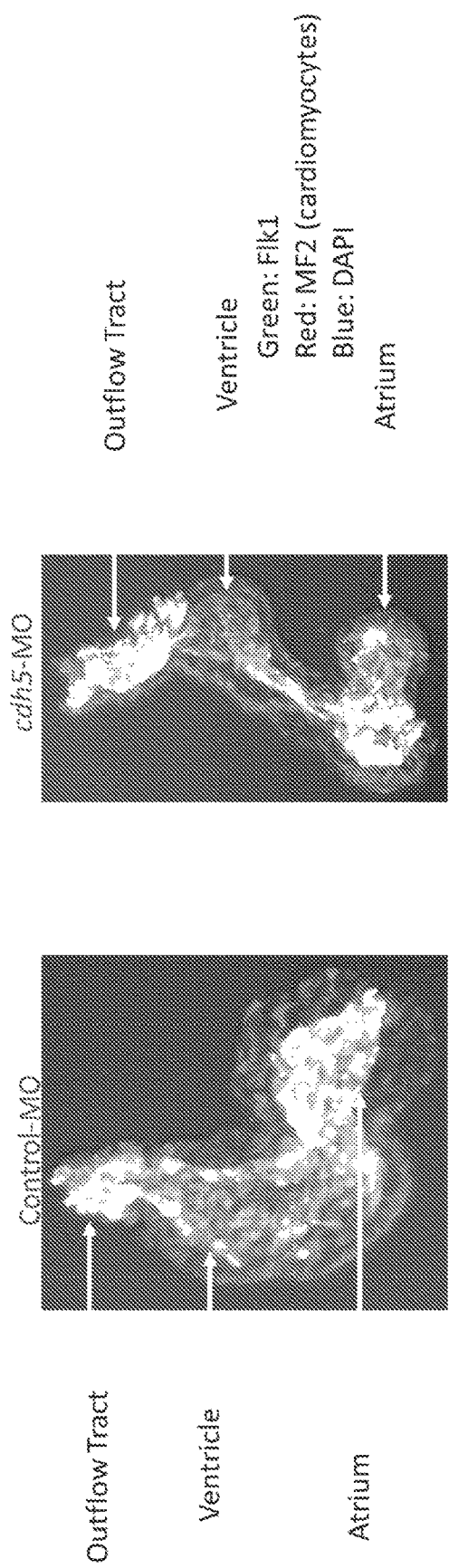
Figure 3A:
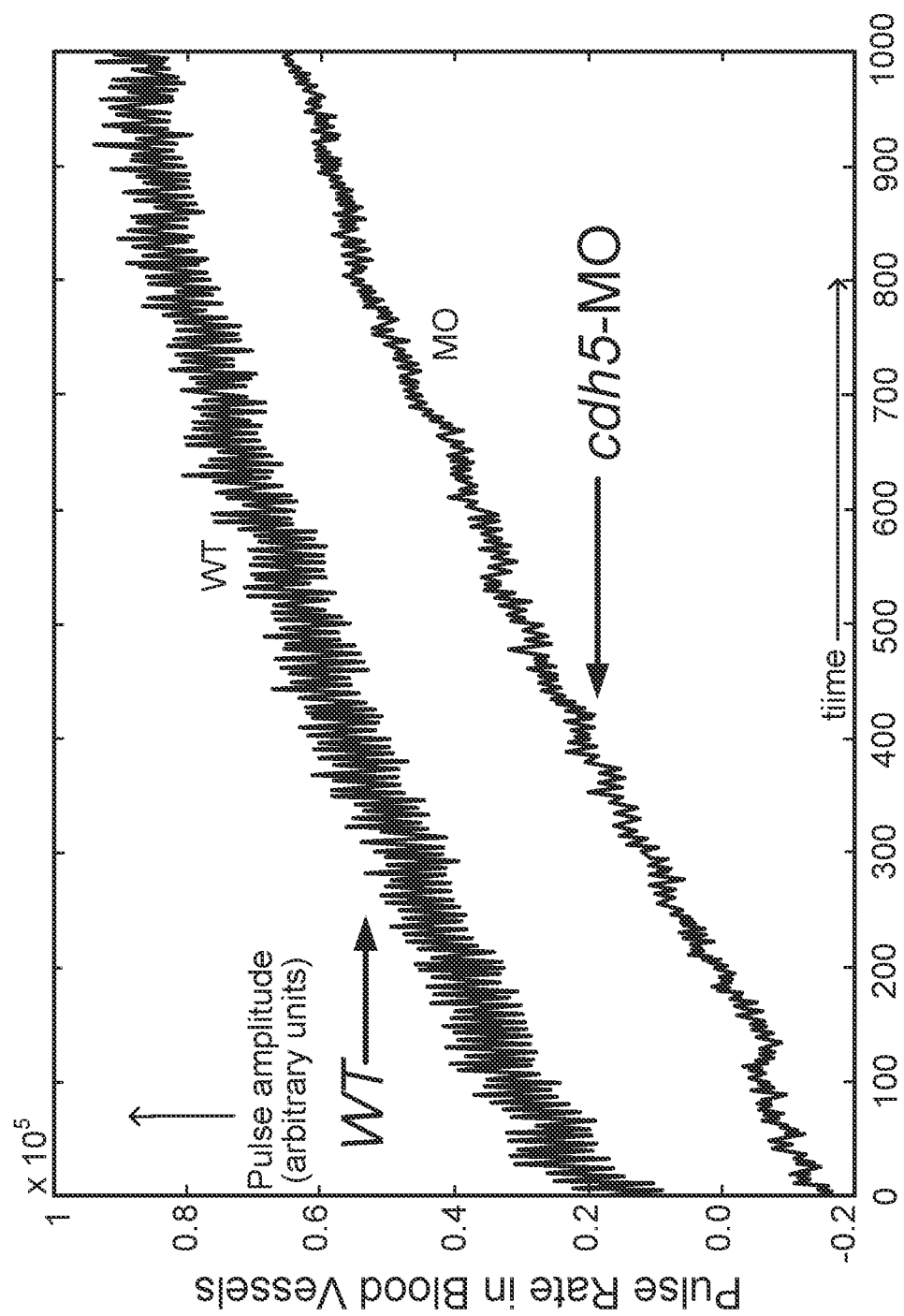
FIGS. 3A-C. Pulsation in blood vessels is due to heartbeat. (A) 3D Doppler analysis to measure pulse rate in wild-type and cdh5-morphant embryos, demonstrating that cdh5-morphants have normal pulse rate in the absence of blood flow. (B-C) Time-lapse confocal imaging of lcr: eGFP::flk1:mCherry in control embryos, followed by machine-learning (artificial intelligence) based measurement of motion-frequency correlation values of pulsating blood vessel, demonstrating that pulsation in blood vessels is synchronized with heartbeat and blood flow.

To begin analyzing the morphology and function of the two-chamber heart in the cdh5-silenced zebrafish embryo, we performed micro-angiography, immunohistochemistry, echocardiography, and electrophysiology assessment of the cdh5-morphant heart. We used electrophysiology and echocardiography to demonstrate that heart rate in the cdh5-morphant was comparable to the control (FIG. 2A), but stroke volume was near null in cdh5-morphants. We, therefore, found that cardiac output (=stroke volume X heartrate) was impaired in cdh5-morphants as well (FIG. 2B). We injected fluorescent beads into the hearts of the cdh5-morphants and followed their passage. Unlike the control embryos, we found that the fluorescent beads did not enter into the main aortic circulation in the cdh5-morphant embryos because they were trapped in the heart (FIG. 2C-D). To examine the structural integrity of the heart, we isolated hearts from the control and cdh5-silenced flk1:mCherr:cmlc2:eGFP embryos and performed immunohistochemistry for endothelial lining (GFP) and cardio-myocytes (MF20). We found that the atrium, atrioventricular (AV) valve, ventricle, and outflow tract are formed in cdh5-morphants, are contracting, but are elongated and distorted (FIG. 2E). In addition, we observed a significant pericardial edema in cdh5-morphant cardiac cavities, which may be due to the back-flow of blood from the heart (FIG. 2C). The accumulation of fluid in the pericardial space results in a reduced ventricular filling and a subsequent hemodynamic compromise (19, 20). To examine whether cardiac tamponade is a factor in the accumulation of fluid in the pericardial space, we punctured the cardiac cavity (as in pericardiocentesis) and aspirated pericardial fluid to reduce the fluid-pressure buildup on the heart. However, we could not rescue the cardiac output deficiency of the cdh5-morphant heart (video data not shown). These data demonstrate that heartbeat is normal in cdh5-morphants, but their cardiac output is impaired due to structural defects in the heart, resulting in accumulation of blood in the pericardial cavity.

Although the heart was beating and blood vessels had formed, cardiac output was near zero and blood cells were not actively circulating in blood vessels. Thus we focused on shear stress-independent biomechanical cues stimulating HSC emergence in blood vessels. Surprisingly, we found that blood vessels were pulsatile, despite a lack of blood flow. These striking data led us to investigate whether pulsation in blood vessels is due to their inherent properties, as is seen with lymphatic vessels, or whether it is due to pulse-pressure generated by the heartbeat. Therefore, we used 3D digital Doppler to measure pulsation frequency in the control embryos and the cdh5-morphants. We found normal pulse-frequency, but a lower amplitude in cdh5-morphants compared to the control (FIG. 3A). Since the amplitude of pulse-rate is governed by heartbeat and blood flow, the lower amplitude in the cdh5-morphants was expected due to an absence of blood flow. However, it is believed both the control and cdh5-morphants had optimum pulse frequency to develop circumferential stretch on blood vessels. Thus, cdh5-morphant embryos become a pivot for us to investigate the role of pulse-pressure mediated circumferential stretch on the endothelial emergence of HSCs.

Figures 3B, 3C:
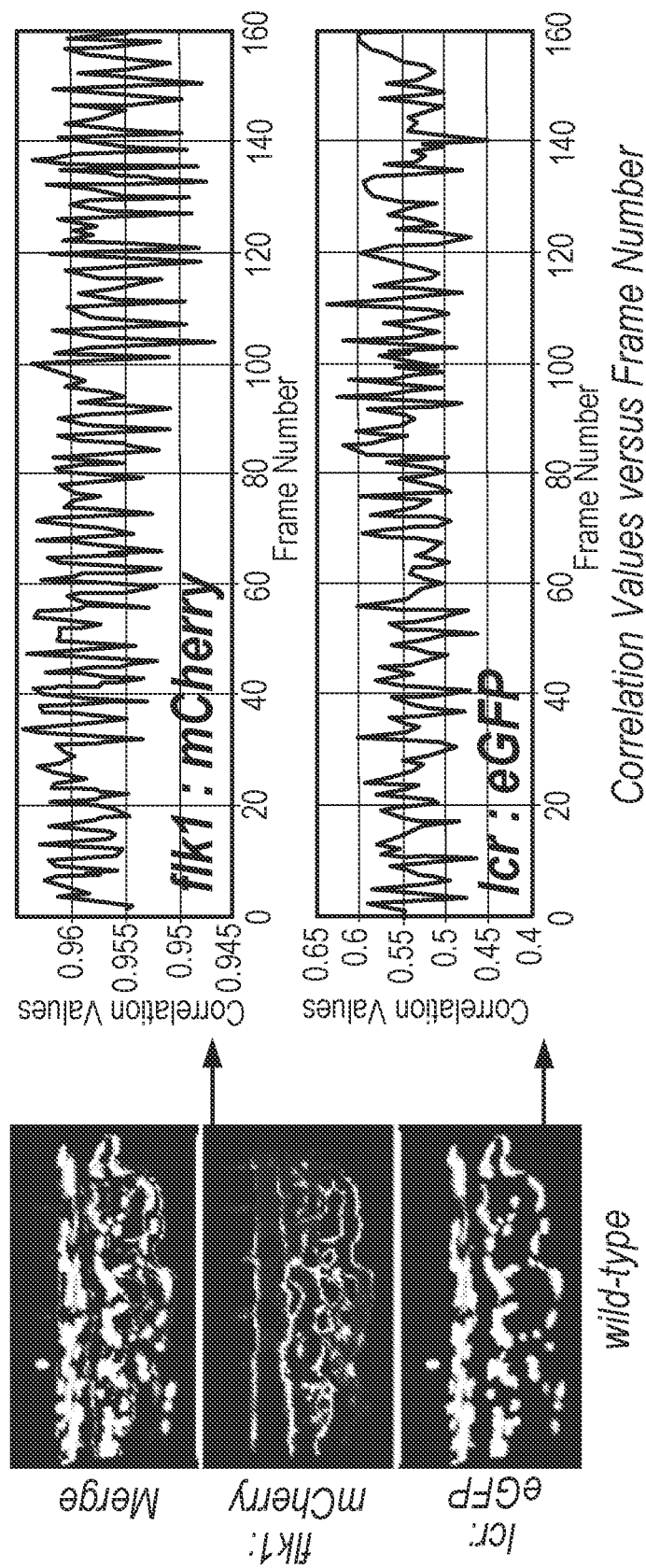
Figure 4:
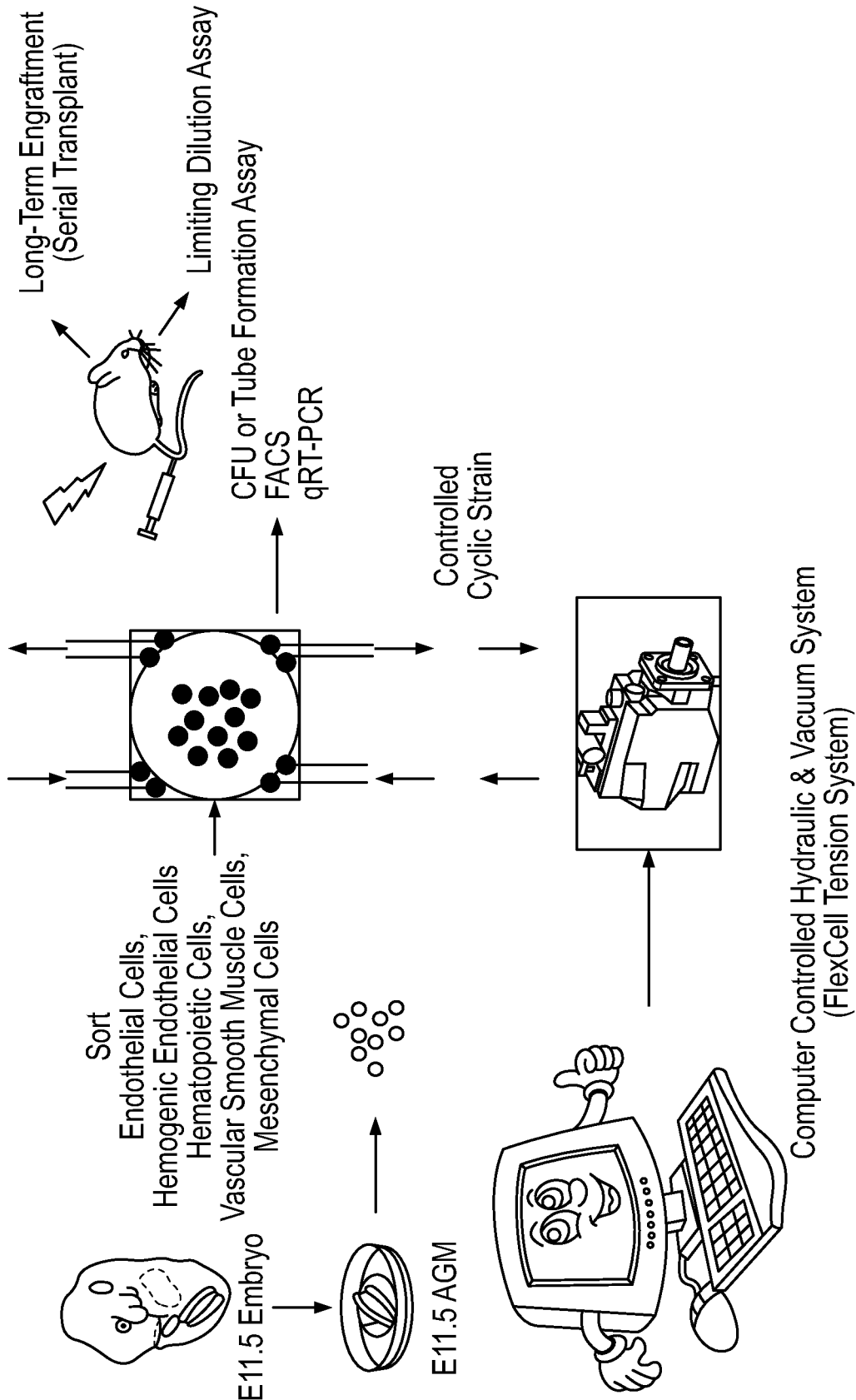
FIG. 4. Schematic representation of recapitulating 2D circumferential stretch conditions on E11.5 AGM-derived sorted endothelial, hemogenic endothelial, vascular, and mesenchymal stromal cells using a standardized, custom-made bioreactor. We use a computer controlled vacuum pump system (FlexCell Tension System) attached to the nylon-membrane of a flexible-bottomed culture plate, followed by analysis of the functional potential of emerging HSC using CFU, gene-expression, FACS, long-term engraftment (including serial transplant), and limiting dilution assays.
Figure 6:
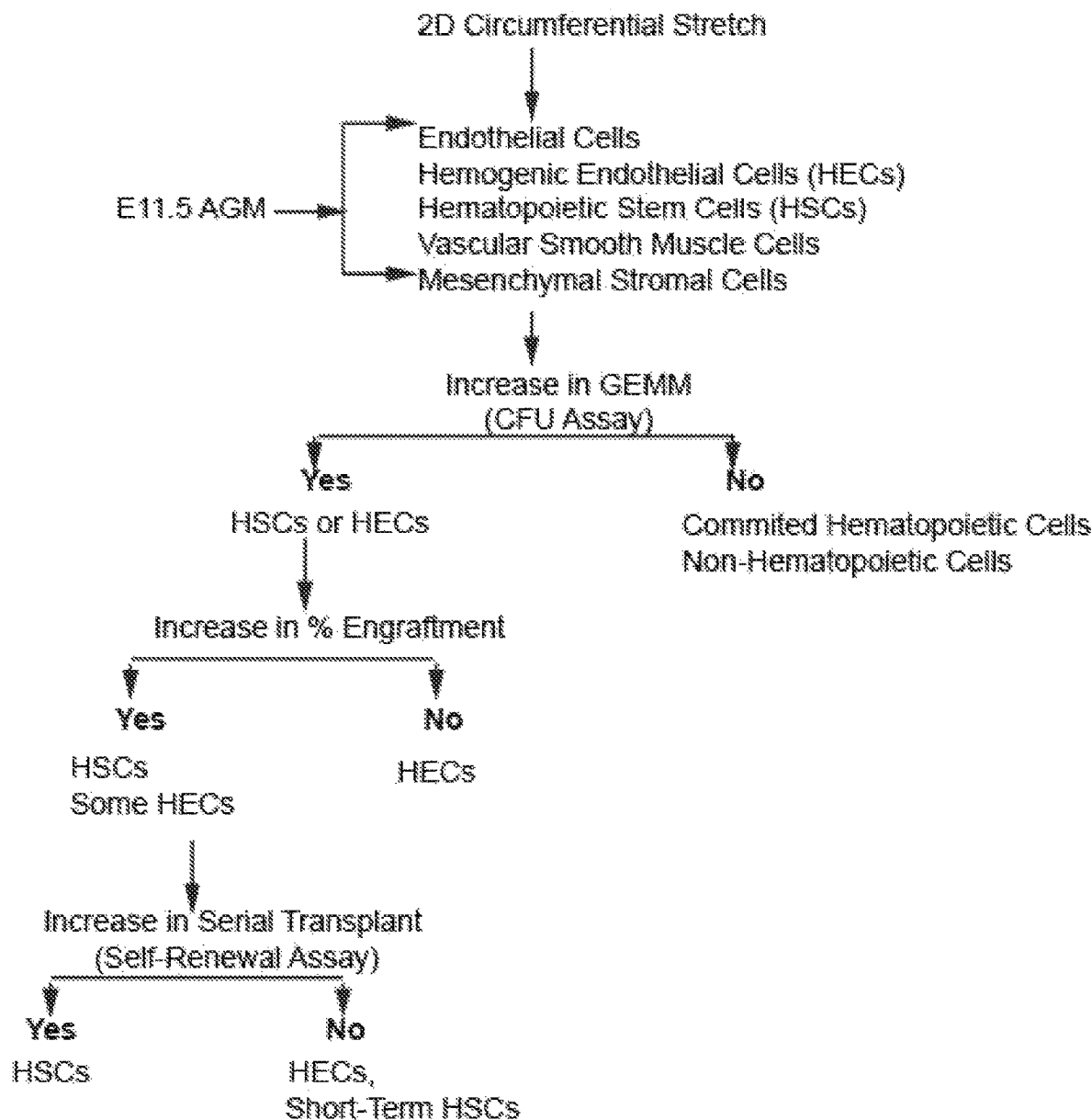
FIG. 6 A decision tree to interpret potential outcomes following 2D circumferential stretch application on E11.5 AGM derived sorted cells.

To document that biomechanical mechanisms independent of circulation and shear stress are active in wild type embryos as well, we performed time-lapse confocal imaging of the pulsating blood vessels in flk1:mCherry::lcr:eGFP embryos to investigate the origin of pulsation and to examine whether pulsation in blood vessels is synchronous with heartbeat (FIG. 3B). We subsequently used machine-learning algorithms (artificial intelligence) to measure individual motion frequency-correlation values from the flk1:mCherry channel, which depicts pulsating blood vessels, and the lcr:eGFP channel, representing red cells in blood circulation (FIG. 3C). When we superimposed motion frequency-correlation values of GFP and mCherry channels, we found that their frequencies overlap. These data eliminate the possibility that pulse is an inherent property of blood vessels. Thus, heartbeat mediated pulse-pressure causes blood vessels to oscillate, which subsequently creates circumferential stretch. Since HSCs emerged in the absence of active blood circulation, we studied the direct effect of circumferential stretch on hemogenic endothelial cells in HSC formation.

In summary, these analyses illustrate that heartbeat and pulse-mediated circumferential stretch stimulate the endothelial emergence of functional HSCs.

Using a customized bioreactor based on organ-on-a-chip (FIG. 4), we applied 2D circumferential stretch (6% cyclic strain, 24 hr) to a single cell suspension of two e.e. E11.5 AGM cells. In parallel, we also incubated two e.e. E11.5 AGM static cells with Trpv4 agonist (GSK101 (29)). We found that both 2D circumferential stretch and Trpv4 agonist treatment not only enhanced GEMM formation, but increased the percentage of engraftment and multi-lineage reconstitution. These data demonstrate that 2D circumferential stretch and the activation of Trpv4 channels on E11.5 AGM-derived cells can enhance functional HSC formation.

Mouse AGM is a heterogeneous tissue. To further dissect the role of circumferential stretch at the cellular level, we sort the endothelial cells, hemogenic endothelial cells, vascular smooth-muscle cells, mesenchymal stromal cells, and hematopoietic cells from E11.5 AGM using fluorescence activated-cell sorting (FACS) or magnetic activated-cell sorting (MACS). We overlay a single cell suspension of each cell type on a FlexCell well, apply 2D circumferential stretch, and analyze CFU formation capacity, gene expression changes (FACS and qRT-PCR), limiting dilution, as well as long-term engraftment and multi-lineage reconstitution capacity, followed by serial transplant assays (FIG. 4, 6).

We also analyze whether the circumferential stretch-mediated endothelial to HSC transition is due to cross-talk between endothelial or hemogenic endothelial cells with VSMCs or mesenchymal cells of the AGM. Therefore, we apply 2D cyclic strain on AGM-derived endothelial cells or hemogenic endothelial cells premixed with VSMCs or mesenchymal cells, followed by HSC functional assays (FIG. 4, 6).

To exclude potential noise from hemogenic endothelial cells engraftment and distinguish between hemogenic endothelial cells and HSCs, we perform a limiting dilution and self-renewal (serial long-term transplant) assays (FIG. 4, 6) using established methods (14, 30-32).

The processes of the hemogenic specification of endothelial cells and the endothelial emergence of HSCs are dynamic and complimentary (13, 14, 24-26). As demonstrated herein, HSCs emerge, develop, engraft, and differentiate in the absence of active blood circulation due to shear stress-independent mechanisms. We have already successfully optimized experimental conditions for recapitulating controlled 2D circumferential stretch conditions on growing cells in the FlexCell Tension System (FIG. 4, 5). Since a heartbeat causes pulsation in blood vessels and thus generates circumferential stretch (FIG. 1-3), an ex vivo reconstitution of circumferential stretch could emerge as a stand-alone, additive, or synergistic cell-extrinsic, biomechanical force stimulating the endothelial transition to HSCs.

Since 2D circumferential stretch on a single cell suspension of E11.5 AGM cells stimulated HSC formation (FIG. 5), 2D circumferential stretch applied to sorted hemogenic endothelial cells is expected to increase HSC formation as well.

The reprogramming of human endothelial cells to hematopoietic cells requires vascular induction (33). Additionally, the vascular niche promotes hematopoietic multipotent progenitor formation (34). Therefore, it is expected that 2D circumferential stretch on endothelial or hemogenic cells pre-mixed with sorted VSMCs would have substantially higher hemogenic impact than 2D circumferential stretch on endothelial or hemogenic endothelial cells alone.

We first differentiate human induced pluripotent stem cell (hiPSC) into embryonic bodies (EBs) and then treat them with drugs and growth factors to induce mesoderm and subsequently hematopoietic and endothelial specification (see Example 3). Between day 7-8 of EB differentiation, we sort CD34+CD43− cells and treat them with drugs and growth factors for seven days to enrich hemogenic endothelial cells. Then we seed human hemogenic endothelial cells (35) on a flexible nylon membrane and test whether 2D ex vivo circumferential stretch stimulates their hematopoietic cell formation potential using CFU assays, gene-expression analyses, and transplant into NOD-SCID immunocompromised mice.

Example 2

Figure 7:
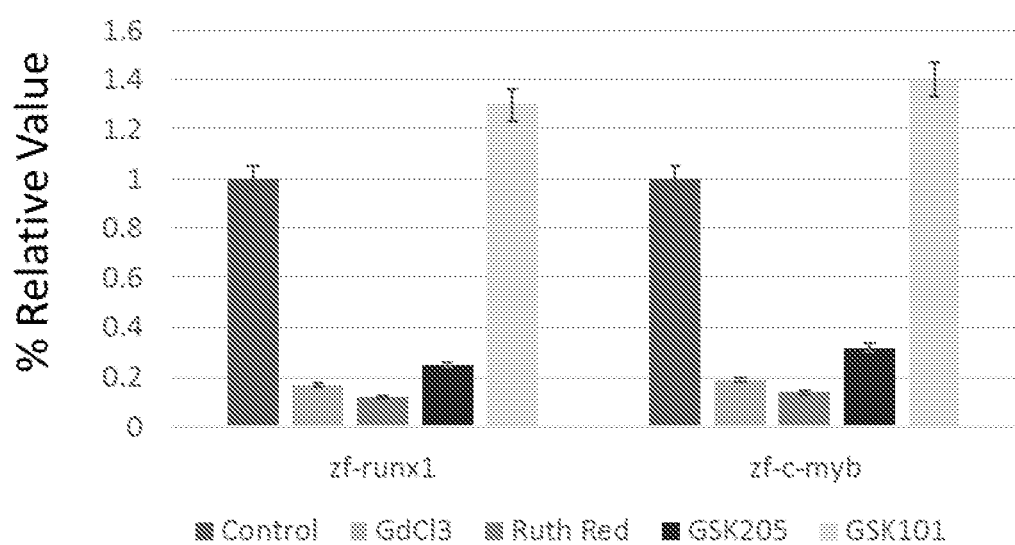
FIG. 7. Inhibition of stretch-activated ion channels reduces HSC formation. qRT-PCR analyses of zf-runx1 and zf-c-Myb expression in GdCl$_3$-, Ruthenium Red-, GSK205 (Trpv4 antagonist)-, and GSK101 (Trpv4 agonist)-treated zebrafish embryos. *P<0.05 vs control; n=120 in each group.
Figure 9A:
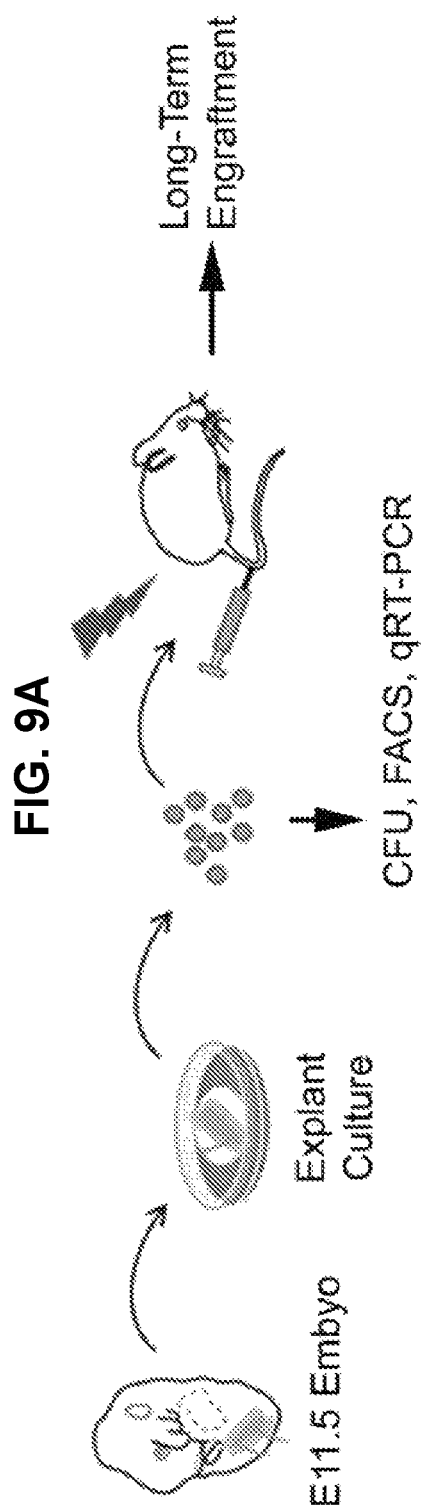
FIGS. 9A-B. Activation of Trpv4 stimulates HSPC formation. (A) Schema of mouse E11.5 AGM-derived hemogenic endothelial cell in explant culture with stretch-sensitive ion channel modulators followed by analyses of their hematopoietic function. (B) We used an explant culture system to incubate whole E11.5 AGM with a non-specific inhibitor of stretch activated ion channel (SAC) (GdC13), pan-inhibitor of Trpv (Ruthenium Red; R.R.), Trpv4 agonist (GSK101 and 4α-PDD), Trpv4 antagonist (GSK205), as well as Trpv4 agonist (GSK101) and CREB phosphorylation inhibitor (KT5720) for 24 hr followed by colony formation assays. We found that activation of Trpv4 stimulates multipotent progenitor (GEMM) formation, whereas inhibition of SAI and Trpv4 attenuates GEMM formation. We also established that inhibition of CREB phosphorylation (KT5720) attenuates stimulating impact of Trpv4 agonist (GSK101) in HSPC formation. n=8; *P<0.05 vs static control; **P<0.05 vs GSK101 treatment.

Examine the Molecular Mechanisms Underlying Trpv4 Signaling During HSC Formation Introduction The impact of circumferential-stretch is communicated by member(s) of the K1-selective family, Trp-family, ENaC/DEG family, and/or Piezo family (36-39). Our gene-expression analyses demonstrate that Trpv4 is expressed in both endothelial and hematopoietic cells. Therefore, we investigated the role of Trpv4 in the endothelial to HSC transition. We demonstrated that the non-specific inhibition of stretch-activated ion channels (40, 41) and Trpv family channel (41, 42), as well as the targeted inhibition of Trpv4 (42) reduced the expression of markers for and numbers of HSPCs in zebrafish and mice (FIG. 7, 9). We also established a functional link between trpv4 signaling and HSC generation, by demonstrating that the activation of trpv4 channels (29) increased HSC formation in zebrafish and mice (FIG. 7, 8A-B, 9) while rescuing hematopoietic deficiency in sih (tnnt2)-silenced embryos, in the absence of heartbeat and blood flow (FIG. 8A, C-D).

We analyze the functional potential of additional HSCs generated following Trpv4 activation by performing zebrafish embryo-to-embryo transplant as well as ex vivo culture of E10.5 mice embryos, followed by long-term engraftment and a multi-lineage reconstitution assay.

It is our expectation that the stimulation of the stretch-activated Trpv4 ion channels will be a giant leap towards exploiting patient-derived endothelial cells as a source of clinical-grade HSCs in the treatment of malignant and non-malignant disorders of blood and bone marrow.

Results

To demonstrate whether the activation of stretch-activated ion channels influences HSC emergence, we incubated zebrafish embryos with a non-specific inhibitor of the stretch-activated ion channels (SAC) (Gadolinium Chloride, GdCl3; (40)) between 19-42 hpf. Using zebrafish WISH and quantitative RT-PCR, we found that the expression of HSPC surrogate markers, runx1 and c-myb, were reduced (FIG. 7) in GdCl$_3$-treated zebrafish embryos. These data demonstrate that cell-signaling triggered by stretch-activated ion channels regulates the endothelial emergence of HSCs.

An impact of circumferential stretch is communicated by member(s) of the K1-selective superfamily, Trp-superfamily, ENaC/DEG superfamily, and/or Piezo family (36-39). In silico gene-expression analyses demonstrated that Trpv4 is expressed in both endothelial and hematopoietic cells. However, the direct role of Trpv4 in HSC emergence has not been established. We therefore treated zebrafish embryos with a pan-inhibitor of Trpv channels (Ruthenium RED; (41)), Trpv4 antagonist (GSK 205; (42)), and Trpv4 agonist (GSK101; (29)) between 19-42 hpf, followed by qRT-PCR and WISH for HSPC surrogate markers (c-myb and runx1). Upon pan-inhibition of the Trpv family channels (using Ruthenium Red (41)), or specific inhibition of Trpv4 (using Trpv4 antagonist; GSK205; (42)), we found a reduction in runx1 and c-myb expression (FIG. 7). We further demonstrated that the incubation of control embryos with trpv4 agonist (GSK101; (29)) increased the expression of HSPC markers, c-myb (FIGS. 7, 8A-B) and runx1. These data implicate the activation of Trpv4 ion channels as key signaling factors in HSC emergence. Together, these findings demonstrate that circumferential stretch stimulates Trpv4 signaling and thus triggers the endothelial emergence of HSCs.

Silent heart cardiac troponin (sih, tnnt2)-mutant embryos lack heartbeat and blood circulation (43). We and others (12) have demonstrated that sih-embryos lack expression of hematopoietic stem progenitor cell (HSPC) markers, such as c-myb (FIG. 8A vs. 8C) and runx1 (data not shown). Because heartbeat-mediated pulse pressure on blood vessels stimulates HSC emergence, we studied whether the activation of the Trpv4 ion channels triggers HSC formation in the absence of a heartbeat and blood circulation. We therefore incubated sih-silenced embryos (casper or cd41:eGFP::flk1:mCherry) with trpv4 agonist (GSK101) between 19-42 hpf. We demonstrated that trpv4 agonist (GSK101) rescues hematopoietic stem progenitor cell (HSPC) formation in sih-embryos based on the mRNA expression levels of runx1 and c-myb using WISH (FIG. 8A, 8C, vs 8D) and qRT-PCR techniques. We also established that trpv4 activation rescues the formation of cd41:eGFP$^+$ HSCs in trpv4-agonist treated sih-silenced cd41-eGFP:flk1-mCherry embryos.

Figure 9B:
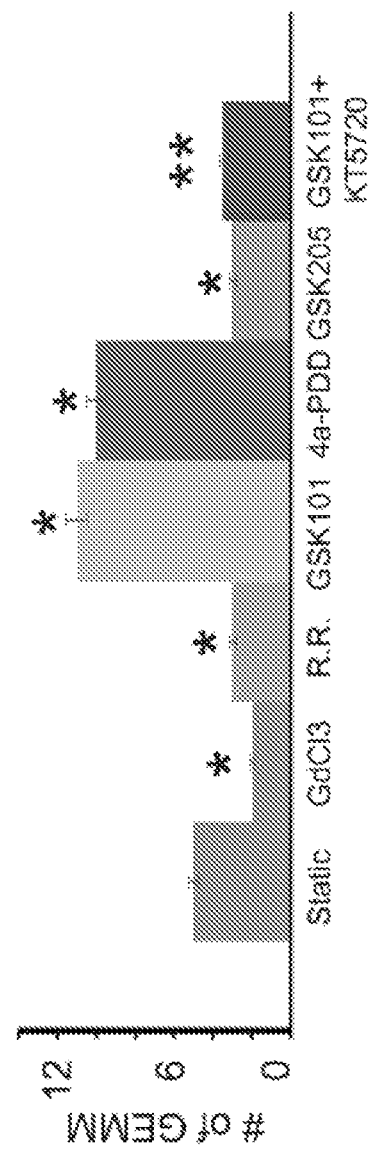
Figure 11:
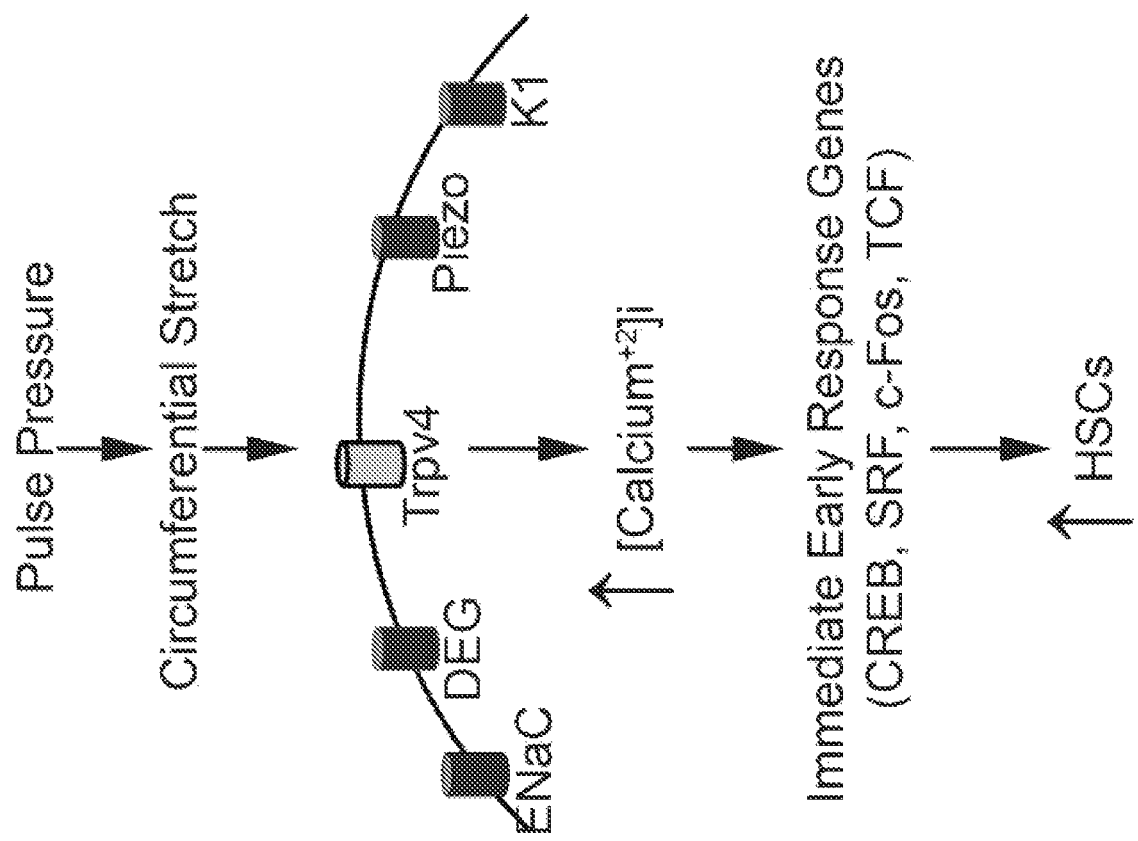
FIG. 11: Proposed mechanism(s) for HSC formation following the Trpv4 activation.

In mice, the first heartbeat occurs at E8.25, and HSCs begin to emerge from AGM-derived hemogenic endothelium between E10.5-E12.5 (10, 11). To investigate whether circumferential stretch-activated ion channels are also involved in mammalian HSC emergence, we incubated E11.5 AGM with non-specific SAC channels inhibitor (GdCl$_3$) and pan-Trpv channel inhibitor (Ruthenium Red) in explant culture media and analyzed their hematopoietic CFU capacity, and the expression of endothelial and hematopoietic genes (CD41, CD45.2, c-Kit, Flk1, CD144). We found that GdC13 and Ruthenium Red reduced the expression of hematopoietic genes (data not shown) and GEMM colony formation capacity (FIG. 9B). These data demonstrate that the circumferential stretch-signaling pathway in HSC emergence and development is conserved in mammalian systems.

To further investigate the influence of Trpv4 on HSC formation from hemogenic endothelial cells, we incubated E11.5 AGM (28) with Trpv4 agonist (GSK101, 4α-PDD (44)) and Trpv4 antagonist (GSK 205) for 24-48 hr (FIG. 9). We found that the pharmacological activation of Trpv4 stimulated multipotent GEMM formation whereas the inhibition of Trpv4 attenuated multipotent GEMM formation (FIG. 9B). These data demonstrate that modulation of the Trpv4 channel regulates the endothelial cell-transition-to HSCs.

In summary, the data highlight that the activation of Trpvr4, a circumferential-stretch signaling molecule, stimulates the endothelial transition to HSCs. Thus, these findings establish the pharmacological activation of Trpv4 as a new avenue to stimulate HSC formation.

Example 2A

Investigate the Functional Utility of HSCs Generated After the Trpv4 Activation

Rationale, Strategies, and Analytical Plan: The circumferential stretch activates trpv4 on endothelial cells (45). Here we demonstrate that circumferential stretch mediated trpv4 activation stimulates the endothelial-to-HSC transition. To show that HSCs produced following Trpv4 activation are functional, we incubate zebrafish embryos with Trpv4 agonists followed by embryo-to-embryo HSC transplant as well as ex vivo incubation of E10.5 mouse embryos with Trpv4 agonists, followed by AGM transplant.

Zebrafish Functional Assays and Embryo-to-Embryo HSC Transplantation:

We utilize zebrafish transgenic lines, cd41:eGFP for HSCs and flk1:mCherry for endothelial cell expression analyses (14). We inject trpv4-morpholino in zebrafish embryos and/or incubate cd41:eGFP::flk1:mCherry transgenic embryos with trpv4 agonists (GSK101, 4a PDD), between 19 and 42 hpf of development. At 42 hpf we will perform a FACS analysis to measure the relative levels of cd41:eGFP$^+$ HSCs, cd41:eGFP$^+$ flk1:mCherry$^+$ hemogenic endothelial cells, and flk1:mCherry$^+$ endothelial cells. In addition, we mount drug-treated or morpholino-injected cd41:eGFP::flk1:mCherry embryos in low-melting point agarose, and perform time-lapse confocal imaging to quantify the cd41:eGFP$^+$ HSCs emerging from flk1:mCherry$^+$ endothelial cells. These analyses examine how the activation or silencing of the trpv4 ion channel pathways could influence the HSC generating capacity of hemogenic endothelial cells. These are established techniques (FIG. 1A-B).

Zebrafish HSC Transplantation: The transplantation of cd41:eGFP$^{low}$ HSCs into irradiated zebrafish embryos has previously successfully contributed to blood progenitors in recipient kidney marrow, demonstrating the functional potential of cd41:eGFP$^{low}$ HSCs (46, 47). To examine the functional potential of HSCs generated after trpv4 activation, we sort cd41:eGFP$^+$ HSCs from trpv4-agonist-treated cd41:eGFP±embryos and prepare a suspension of 400 cells/microliter with 0.5% rhodamine-dextran as a marker for injection. We back-fill a microinjection needle with the cell suspension and calibrate it to ensure each embryo can be injected with 1, 2, or 4 drops. This gives an estimated cell dose of 0.4, 0.8, or 1.6 cells per embryo. We inject the drops into the sinus venosus (i.e., duct of Cuvier) of 48 hpf wild-type embryo recipients, placed in agarose injection ramps. We inject approximately 30 embryos per dose and expect 12-26 embryos per group to survive to adulthood (3-5 months) based on our prior experience. We analyze cd41:eGFP$^+$ platelets in recipient embryos and/or whole-kidney marrow for a percentage of engrafted cd41$^+$ cells using a FACS machine. We score any recipients with GFP$^+$-positive cells above background (>0.001% of WKM) as engrafted. This method has been described previously (14, 48).

Mouse ex vivo Embryo Incubation Systems:

To investigate the factors stimulating the endothelial emergence of HSCs, we have developed an ex vivo mouse embryo culture system to grow mouse embryos from E9.5 to E12.5 by optimizing media and temperature conditions, gaseous mixtures, and the humidity level in our state-of-the-art ex vivo incubation chamber (FIGS. 10A-C). Thus, we treat mouse embryos with pharmacological agents targeting Trpv4 between E9.5 and E12.5 to test their influence on the endothelial emergence of HSCs. These analyses validate the functional HSC-generating efficiency of Trpv4-ion channel modulators (FIG. 10D).

To investigate how Trpv4 influences mammalian HSC formation in ex vivo conditions, we incubate E10.5 or E11.5 mouse embryos with Trpv4 modulators for 24-48 hr (FIGS. 10A-C). Subsequently, we dissect AGM tissue from E11.5 or E12.5 mouse embryos to perform CFU assays, and measure CD41, c-Kit, CD144, and CD45.2 expression using FACS and qRT-PCR analyses (FIG. 10D). We also transplant AGM-derived definitive HSCs into sub-lethally irradiated and/or immunocompromised mice to validate their long-term engraftment as well as multi-lineage reconstitution potential by evaluating the blood-lineage distribution in recipients for up to 16 weeks. To dissect the role of Trpv4 at the cellular level, we sort endothelial, hemogenic endothelial, and hematopoietic cells from E11.5 AGM before transplantation using known CFC assays, FACS and qRT-PCR analyses, and long-term engraftment analyses (14, 30-32, 49, 50).

Example 2B

Molecular Mechanisms Underlying Trpv4 Activation During HSC Development

Rationale and Strategies: Activation of Trpv4 stimulates intracellular calcium levels (51-56). A transient increase in intracellular calcium levels ($[Ca^{+2}]i$) further stimulates immediate early genes class of transcription factors (57, 58), such as CREB (38, 59-61), Fos/Jun (62-64), SRF/Elk 1 (57, 65), NFAT(66, 67), TCF(68, 69), TGF-β1/MRTF-A (63). Since Trpv4 activation stimulates the endothelial-to-HSC formation (FIG. 5, 7-9), we investigate how the Trpv4 signaling modulates cellular ion levels and transcriptional changes in the endothelial cell fate specification to HSCs.

Our incubation of human umbilical vein endothelial cells (HUVEC) withTrpv4 agonist (GSK101) resulted in increase in $[Ca^{+2}]i$ levels. To analyze whether Trpv4 and CREB cross-talk during the endothelial to HSC transition, we used E11.5 AGM explant culture (FIG. 9A) and found that pharmacological inhibition of CREB phosphorylation (using KT5720; (70)) attenuated Trpv4 agonist-mediated increase in multipotent GEMM formation (FIG. 9B).

To establish the functional correlations between Trpv4 activation, $[Ca^{+2}]I$, CREB phosphorylation, and/or additional transcriptional factor during HSC formation, we incubate zebrafish and/or mouse embryos with Trpv4 agonist and specific transcription factor inhibitor (FIGS. 9B, 10). We perform qRT-PCR, whole-mount in situ, and time-lapse confocal imaging in zebrafish embryos as well as CFU, FACS, and long-term engraftment assays for AGM cells derived from drug-treated E11.5 mouse embryos.

These results provide the first evidence for the direct role of Trpv4 in the endothelial emergence of functional HSCs. Since we demonstrated that E11.5 AGM treatment with Trpv4 agonist stimulates functional HSC formation, it is reasonable to expect that cd41:eGFP+ HSCs generated after Trpv4 activation would engraft and thus would be functional. Similarly, our ex vivo incubation of E10.5 mouse embryos with Trpv4 agonists followed by transplant could also demonstrate higher levels of functional HSC formation. As incubation of zebrafish embryos with trpv4 agonist increased HSPC gene expression, incubation of mouse embryos and/or whole AGM would produce increased functional HSC formation, resulting in increased GEMM formation, hematopoietic gene expression, as well as higher long-term engraftment and multi-lineage reconstitution. Since Trpv4 activation enhances $[Ca^{+2}]i$ levels in HUVECs, we would see an increase in $[Ca+^2]i$ levels in Trpv4-agonist treated hemogenic endothelial cells. IEGs are activated by a transient increase in intracellular calcium levels (57, 58). Therefore, we expect to see increased phosphorylation of CREB (FIG. 9B) and/or higher expression/activity of other IEGs in Trpv4-activated hemogenic endothelial cells. Thus, the zebrafish and mouse-based complimentary approaches could establish a conserved role of Trpv4 in functional HSC emergence and development. We combine genetic and pharmacological tools with explant and ex vivo mouse embryo culture methods to demonstrate the promising utility of Trpv4 and/or IEG modulators in establishing endothelial cells as a source of functional HSCs in the treatment of human hematologic diseases.

Example 3

Exemplary Protocol for Generation of HE Cells from Human iPSC

The following protocol is based on the publication Ditadi et al., Nat Cell Biol. 2015;17(5):580-91.
  Aggregation Media D0-D2
    375 ml IMDM (Invitrogen 10639-011)
    125 ml Ham's F-12
    5 ml P/S (10 ng/ml)
    5 ml N2 (LifeTech 17502-048)
    10 ml B27 (LifeTech 17504-044)
    3.3 ml BSA (0.05%; stock 7.5%, stored at +4° C.)
    (5 ml L-glutamin (2 mM); usually supplemented in the IMDM)
    880 uL Ascorbic Acid (1 mM; 100 mg/mL stock (0.57 M) in $H_2O$, stored at −20° C.)
    750 uL Holo-Transferrin (150 ug/ml; Sigma T0665-1G; 100 mg/ml stock in IMDM, stored at −20° C.)
    1 mL MTG 500× (0.4 mM; prepare 500× stock: 35 uL/2 ml PBS, filter sterilized, stored at receiving +4° C.)
  hEB Media from D3
    500 ml StemPro-34 with Supplement (Invitrogen 10639-011)
    5 ml L-glutamin (2 mM)
    880 uL Ascorbic Acid (1 mM; 100 mg/mL stock (0.57 M) in $H_2O$, stored at −20° C.)
    750 uL Holo-Transferrin (150 ug/ml; Sigma T0665-1G; 100 mg/ml stock in IMDM, stored at −20° C.)
    1 mL MTG 500× (0.4 mM; prepare 500× stock: 35 uL/2 ml PBS, filter sterilized, stored at receiving +4° C.)
    5 ml P/S (10 ng/ml)
  D0. Generation of EBs
    1) Generally, one week after splitting hiPSCs, cells are ready to make EBs. Colonies should appear thick, dense, white and fairly free of differentiation.
    2) Aspirate media from each 15 cm dish. Replace with 8 mL of 1× collagenase IV diluted in 0.22 uM filtered DMEM/F12
      Collagenase IV (Gibco Cat #17104-019) Receiving fridge.
      Measure out 0.5 g collagenase IV and dilute with 50 mL DMEM/F12.
      Filter with 0.22 uM steriflip (500 mg/50 mL=10×). Before use, dilute
      10× collagenase with DMEM/F12 to 1× (1 mg/mL).
    3) Incubate at room temperature in the hood for 5 minutes.
    4) Aspirate collagenase IV and replace with 8 mL of filtered DMEM/F12.
    5) Using a cell scraper, scrape colonies only once, taking care to preserve the entire colony.
    6) Gently and slowly transfer the cells to a Falcon-15 tube using a 5 mL glass pipet. If there are residual colonies, wash plates with additional 5 mL and add to same Falcon-15.
    7) Allow cells to settle in the Falcon-15 by gravity (~3-5 minutes). Aspirate the supernatant to get rid of most of the MEFs that remain in suspension. Gently add ~10 mL of DMEM/F12 to wash cells, and spin down 1000 rpm for 1 min.

8) While cells are spinning, add 11 mL of Aggregation media to Low-Adherent 10 cm dishes.
9) Aspirate the media and resuspend cells gently with 1 mL of Aggregation media.
10) Gently transfer the 1 mL of cells to each Low-Adherent 10 cm containing Aggregation media. Using the same pipette, pipet up 1 mL from an area of the plate without any cells and wash the Falcon-15. Add back the 1 mL to the Falcon-15; final volume of each plate now containing 2 starting plates of hiPSCs is 12 mL.
11) Transfer to hypoxic incubator at 37° C. 4-5 plates can be stacked on top of one another, with one plate filled with PBS at the bottom of the stack to prevent evaporation. This is day 0 of hEB culture.

D0. Add 10 ng/ml BMP4. Culture under hypoxia (5% CO2/5% O2/90% N2) for days 0-8.

D1. 10 ng/ml BMP4+5 ng/ml bFGF. Add directly to media.

D2. 10 ng/ml BMP4+5 ng/ml bFGF+6 µA4 SB-431542+3 µM CHIR99021. Add directly to media, unless color has changed or there is a lot of cell debris.

D3. 5 ng/ml bFGF+15 ng/ml VEGF. Collect media, spin 1 min 1,000 rpm, replace media with hEB media.

D4-5. 5 ng/ml bFGF+15 ng/ml VEGF. Add directly to media.

D6-7. 5 ng/ml bFGF+15 ng/ml VEGF+10 ng/ml IL-6+5 ng/ml IL-11+25 ng/ml IGF-1+50 ng/ml SCF+2 U/ml final EPO. Collect media, spin 1 min 1,000 rpm, replace media with hEB media and hematopoietic cytokines.

D8. 5 ng/ml bFGF+15 ng/ml VEGF+10 ng/ml IL-6+5 ng/ml IL-11+25 ng/ml IGF-1+50 ng/ml SCF+2 U/ml final EPO+30 ng/ml+TPO+10 ng/ml Flt-3L+30 ng/ml IL-3

D9. 5 ng/ml bFGF+15 ng/ml VEGF+10 ng/ml IL-6+5 ng/ml IL-11+25 ng/ml IGF-1+50 ng/ml SCF+2 U/ml final EPO+30 ng/ml+TPO+10 ng/ml Flt-3L+30 ng/ml IL-3. Move cells to normal O2 incubator

TABLE 1

Cell Treatment Protocol

| Day 0 | Day 1 | Day 2 | Day 3 | Day 4 | Day 5 | Day 6 | Day 7 | Day 8 | Day 9 |
|---|---|---|---|---|---|---|---|---|---|
| BMP4 | BMP4 | BMP4 | bFGF | bFGF | bFGF | bFGF | bFGF | bFGF | bFGF |
|  | bFGF | bFGF | VEGF | VEGF | VEGF | VEGF | VEGF | VEGF | VEGF |
|  |  | SB |  |  |  |  |  |  |  |
|  |  | CHIR |  |  |  |  |  |  |  |
|  |  |  |  |  |  | IL-6 | IL-6 | IL-6 | IL-6 |
|  |  |  |  |  |  | IL-11 | IL-11 | IL-11 | IL-11 |
|  |  |  |  |  |  | IGF-1 | IGF-1 | IGF-1 | IGF-1 |
|  |  |  |  |  |  | SCF | SCF | SCF | SCF |
|  |  |  |  |  |  | EPO | EPO | EPO | EPO |
|  |  |  |  |  |  |  |  | TPO | TPO |
|  |  |  |  |  |  |  |  | Flt-3 | Flt-3 |
|  |  |  |  |  |  |  |  | IL-3 | IL-3 |

REFERENCES CITED

1. Shimamura A. Clinical approach to marrow failure. Hematology/the Education Program of the American Society of Hematology American Society of Hematology Education Program. 2009:329-37.

2. Shimamura A, Alter B P. Pathophysiology and management of inherited bone marrow failure syndromes. Blood Rev. 2010;24(3):101-22.

3. Burt R K, Loh Y, Pearce W, Beohar N, Barr W G, Craig R, Wen Y, Rapp J A, Kessler J. Clinical applications of blood-derived and marrow-derived stem cells for nonmalignant diseases. JAMA. 2008; 299(8):925-36.

4. Syres K, Harrison F, Tadlock M, Jester J V, Simpson J, Roy S, Salomon D R, Cherqui S. Successful treatment of the murine model of cystinosis using bone marrow cell transplantation. Blood. 2009; 114(12):2542-52.

5. Rebeiro P, Moore J. The role of autologous haemopoietic stem cell transplantation in the treatment of autoimmune disorders. Intern Med J. 2015.

6. Or-Geva N, Reisner Y. Megadose stem cell administration as a route to mixed chimerism. Curr Opin Organ Transplant. 2014; 19(4):334-41.

7. Chang Y J, Huang X J. Haploidentical SCT: the mechanisms underlying the crossing of HLA barriers. Bone Marrow Transplant. 2014; 49(7):873-9.

8. Blade J, Samson D, Reece D, Apperley J, Bjorkstrand B, Gahrton G, Gertz M, Giralt S, Jagannath S, Vesole D. Criteria for evaluating disease response and progression in patients with multiple myeloma treated by high-dose therapy and haemopoietic stem cell transplantation. Myeloma Subcommittee of the EBMT. European Group for Blood and Marrow Transplant. Br J Haematol. 1998; 102(5):1115-23. PubMed PMID: 9753033.

9. Pavletic S Z, Khouri I F, Haagenson M, King R J, Bierman P J, Bishop M R, Carston M, Giralt S, Molina A, Copelan E A, Ringden O, Roy V, Ballen K, Adkins D R, McCarthy P, Weisdorf D, Montserrat E, Anasetti C. Unrelated donor marrow transplantation for B-cell chronic lymphocytic leukemia after using myeloablative conditioning: results from the Center for International Blood and Marrow Transplant research. J Clin Oncol. 2005; 23(24):5788-94.

10. Dzierzak E, Speck N A. Of lineage and legacy: the development of mammalian hematopoietic stem cells. Nat Immunol. 2008; 9(2):129-36.

11. Orkin S H, Zon L I. Hematopoiesis: an evolving paradigm for stem cell biology. Cell. 2008; 132(4):631-44.

12. North T E, Goessling W, Peeters M, Li P, Ceol C, Lord A M, Weber G J, Harris J, Cutting C C, Huang P, Dzierzak E, Zon L I. Hematopoietic stem cell development is dependent on blood flow. Cell. 2009; 137(4):736-48.

13. Adamo L, Naveiras O, Wenzel P L, McKinney-Freeman S, Mack P J, Gracia-Sancho J, Suchy-Dicey A, Yoshimoto M, Lensch M W, Yoder M C, Garcia-Cardena G, Daley G Q. Biomechanical forces promote embryonic haematopoiesis. Nature. 2009; 459(7250):1131-5.

14. Anderson H, Patch T C, Reddy P N, Hagedorn E J, Kim P G, Soltis K A, Chen M J, Tamplin O J, Frye M, MacLean G A, Hubner K, Bauer D E, Kanki J P, Vogin G, Huston N C, Nguyen M, Fujiwara Y, Paw B H, Vestweber D, Zon L I, Orkin S H, Daley G Q, Shah D I. Hematopoietic stem cells develop in the absence of endothelial cadherin 5 expression. Blood. 2015.

15. Locasciulli A, Oneto R, Bacigalupo A, Socie G, Korthof E, Bekassy A, Schrezenmeier H, Passweg J, Fuhrer M, Severe Aplastic Anemia Working Party of the European B, Marrow Transplant G. Outcome of patients with acquired aplastic anemia given first line bone marrow transplantation or immunosuppressive treatment in the last decade: a report from the European Group for Blood and Marrow Transplantation (EBMT). Haematologica. 2007; 92(1):11-8. PubMed PMID: 17229630.

16. Carmeliet P, Lampugnani M G, Moons L, Breviario F, Compernolle V, Bono F, Balconi G, Spagnuolo R, Oosthuyse B, Dewerchin M, Zanetti A, Angellilo A, Mattot V, Nuyens D, Lutgens E, Clotman F, de Ruiter M C, Gittenberger-de Groot A, Poelmann R, Lupu F, Herbert J M, Collen D, Dejana E. Targeted deficiency or cytosolic truncation of the VE-cadherin gene in mice impairs VEGF-mediated endothelial survival and angiogenesis. Cell. 1999; 98(2):147-57. PubMed PMID: 10428027.

17. Giannotta M, Trani M, Dejana E. VE-cadherin and endothelial adherens junctions: active guardians of vascular integrity. Developmental cell. 2013; 26(5):441-54.

18. Vittet D, Buchou T, Schweitzer A, Dejana E, Huber P. Targeted null-mutation in the vascular endothelial-cadherin gene impairs the organization of vascular-like structures in embryoid bodies. Proceedings of the National Academy of Sciences of the United States of America. 1997; 94(12): 6273-8. PubMed PMID: 9177207; PMCID: 21039.

19. Spodick D H. Acute cardiac tamponade. N Engl J Med. 2003; 349(7):684-90.

20. Isselbacher E M, Cigarroa J E, Eagle K A. Cardiac tamponade complicating proximal aortic dissection. Is pericardiocentesis harmful? Circulation. 1994; 90(5):2375-8. PubMed PMID: 7955196.

21. Chen M J, Yokomizo T, Zeigler B M, Dzierzak E, Speck N A. Runx1 is required for the endothelial to haematopoietic cell transition but not thereafter. Nature. 2009; 457(7231):887-91.

22. Clarke R L, Yzaguirre A D, Yashiro-Ohtani Y, Bondue A, Blanpain C, Pear W S, Speck N A, Keller G. The expression of Sox17 identifies and regulates haemogenic endothelium. Nat Cell Biol. 2013; 15(5):502-10.

23. Swiers G, Rode C, Azzoni E, de Bruijn M F. A short history of hemogenic endothelium. Blood cells, molecules & diseases. 2013; 51(4):206-12.

24. Schmitt C E, Lizama C O, Zovein A C. From transplantation to transgenics: mouse models of developmental hematopoiesis. Exp Hematol. 2014; 42(8):707-16.

25. Zape J P, Zovein A C. Hemogenic endothelium: origins, regulation, and implications for vascular biology. Seminars in cell & developmental biology. 2011; 22(9): 1036-47.

26. Zovein A C, Hofmann J J, Lynch M, French W J, Turlo K A, Yang Y, Becker M S, Zanetta L, Dejana E, Gasson J C, Tallquist M D, Iruela-Arispe M L. Fate tracing reveals the endothelial origin of hematopoietic stem cells. Cell Stem Cell. 2008; 3(6):625-36.

27. Tober J, Yzaguirre A D, Piwarzyk E, Speck N A. Distinct temporal requirements for Runx1 in hematopoietic progenitors and stem cells. Development. 2013; 140(18): 3765-76.

28. Taoudi S, Morrison A M, Inoue H, Gribi R, Ure J, Medvinsky A. Progressive divergence of definitive haematopoietic stem cells from the endothelial compartment does not depend on contact with the foetal liver. Development. 2005; 132(18):4179-91.

29. Jin M, Wu Z, Chen L, Jaimes J, Collins D, Walters E T, O'Neil R G. Determinants of TRPV4 activity following selective activation by small molecule agonist GSK1016790A. PloS one. 2011; 6(2):e16713.

30. Arora N, Wenzel P L, McKinney-Freeman S L, Ross S J, Kim P G, Chou S S, Yoshimoto M, Yoder M C, Daley G Q. Effect of developmental stage of HSC and recipient on transplant outcomes. Developmental cell. 2014; 29(5):621-8.

31. Doulatov S, Vo L T, Chou S S, Kim P G, Arora N, Li H, Hadland B K, Bernstein I D, Collins J J, Zon L I, Daley G Q. Induction of multipotential hematopoietic progenitors from human pluripotent stem cells via respecification of lineage-restricted precursors. Cell Stem Cell. 2013; 13(4): 459-70.

32. Kim P G, Albacker C E, Lu Y F, Jang I H, Lim Y, Heffner G C, Arora N, Bowman T V, Lin M I, Lensch M W, De Los Angeles A, Zon L I, Loewer S, Daley G Q. Signaling axis involving Hedgehog, Notch, and Scl promotes the embryonic endothelial-to-hematopoietic transition. Proc Natl Acad Sci USA. 2013; 110(2):E141-50.

33. Sandler V M, Lis R, Liu Y, Kedem A, James D, Elemento O, Butler J M, Scandura J M, Rafii S. Reprogramming human endothelial cells to haematopoietic cells requires vascular induction. Nature. 2014; 511(7509):312-8.

34. Gori J L, Butler J M, Chan Y Y, Chandrasekaran D, Poulos M G, Ginsberg M, Nolan D J, Elemento O, Wood B L, Adair J E, Rafii S, Kiem H P. Vascular niche promotes hematopoietic multipotent progenitor formation from pluripotent stem cells. J Clin Invest. 2015; 125(3):1243-54.

35. Ditadi A, Sturgeon C M, Tober J, Awong G, Kennedy M, Yzaguirre A D, Azzola L, Ng E S, Stanley E G, French D L, Cheng X, Gadue P, Speck N A, Elefanty A G, Keller G. Human definitive haemogenic endothelium and arterial vascular endothelium represent distinct lineages. Nat Cell Biol. 2015; 17(5):580-91.

36. Pathak M M, Nourse J L, Tran T, Hwe J, Arulmoli J, Le D T, Bernardis E, Flanagan L A, Tombola F. Stretch-activated ion channel Piezo1 directs lineage choice in human neural stem cells. Proceedings of the National Academy of Sciences of the United States of America. 2014; 111(45): 16148-53.

37. Tavernarakis N, Driscoll M. Mechanotransduction in Caenorhabditis elegans: the role of DEG/ENaC ion channels. Cell Biochem Biophys. 2001; 35(1):1-18.

38. Yin J, Kuebler W M. Mechanotransduction by TRP channels: general concepts and specific role in the vasculature. Cell Biochem Biophys. 2010; 56(1):1-18.

39. Del Valle M E, Cobo T, Cobo J L, Vega J A. Mechanosensory neurons, cutaneous mechanoreceptors, and putative mechanoproteins. Microsc Res Tech. 2012; 75(8): 1033-43.

40. Laine M, Arjamaa O, Vuolteenaho O, Ruskoaho H, Weckstrom M. Block of stretch-activated atrial natriuretic peptide secretion by gadolinium in isolated rat atrium. J Physiol. 1994; 480 (Pt 3):553-61. PubMed PMID: 7869268; PMCID: 1155828.

41. Park J H, Lee S, Cho D H, Park Y M, Kang D H, Jo I. Far-infrared radiation acutely increases nitric oxide production by increasing Ca(2+) mobilization and Ca(2+)/calmodulin-dependent protein kinase II-mediated phosphorylation of endothelial nitric oxide synthase at serine 1179. Biochem Biophys Res Commun. 2013; 436(4):601-6.

42. Phan M N, Leddy H A, Votta B J, Kumar S, Levy D S, Lipshutz D B, Lee S H, Liedtke W, Guilak F. Functional characterization of TRPV4 as an osmotically sensitive ion channel in porcine articular chondrocytes. Arthritis Rheum. 2009; 60(10):3028-37.

43. Sehnert A J, Huq A, Weinstein B M, Walker C, Fishman M, Stainier D Y. Cardiac troponin T is essential in sarcomere assembly and cardiac contractility. Nature genetics. 2002; 31(1):106-10.

44. Alexander R, Kerby A, Aubdool A A, Power A R, Grover S, Gentry C, Grant A D. 4alpha-phorbol 12,13-didecanoate activates cultured mouse dorsal root ganglia neurons independently of TRPV4. Br J Pharmacol. 2013; 168(3):761-72.

45. Thodeti C K, Matthews B, Ravi A, Mammoto A, Ghosh K, Bracha A L, Ingber D E. TRPV4 channels mediate cyclic strain-induced endothelial cell reorientation through integrin-to-integrin signaling. Circ Res. 2009; 104(9):1123-30.

46. Ma D, Zhang J, Lin H F, Italiano J, Handin R I. The identification and characterization of zebrafish hematopoietic stem cells. Blood. 2011; 118(2):289-97.

47. Tamplin O J, Durand E M, Can L A, Childs S J, Hagedorn E J, Li P, Yzaguirre A D, Speck N A, Zon L I. Hematopoietic stem cell arrival triggers dynamic remodeling of the perivascular niche. Cell. 2015; 160(1-2):241-52.

48. Li P, Lahvic J L, Binder V, Pugach E K, Riley E B, Tamplin O J, Panigrahy D, Bowman T V, Barrett F G, Heffner G C, McKinney-Freeman S, Schlaeger T M, Daley G Q, Zeldin D C, Zon L I. Epoxyeicosatrienoic acids enhance embryonic haematopoiesis and adult marrow engraftment. Nature. 2015; 523(7561):468-71.

49. Lux C T, Yoshimoto M, McGrath K, Conway S J, Palis J, Yoder M C. All primitive and definitive hematopoietic progenitor cells emerging before E10 in the mouse embryo are products of the yolk sac. Blood. 2008; 111(7):3435-8.

50. Rhodes K E, Gekas C, Wang Y, Lux C T, Francis C S, Chan D N, Conway S, Orkin S H, Yoder M C, Mikkola H K. The emergence of hematopoietic stem cells is initiated in the placental vasculature in the absence of circulation. Cell stem cell. 2008; 2(3):252-63.

51. Denadai-Souza A, Martin L, de Paula M A, de Avellar M C, Muscara M N, Vergnolle N, Cenac N. Role of transient receptor potential vanilloid 4 in rat joint inflammation. Arthritis Rheum. 2012; 64(6):1848-58.

52. D'Aldebert E, Cenac N, Rousset P, Martin L, Rolland C, Chapman K, Selves J, Alric L, Vinel J P, Vergnolle N. Transient receptor potential vanilloid 4 activated inflammatory signals by intestinal epithelial cells and colitis in mice. Gastroenterology. 2011; 140(1):275-85.

53. Ducret T, Guibert C, Marthan R, Savineau J P. Serotonin-induced activation of TRPV4-like current in rat intrapulmonary arterial smooth muscle cells. Cell Calcium. 2008; 43(4):315-23.

54. Randhawa P K, Jaggi A S. TRPV4 channels: physiological and pathological role in cardiovascular system. Basic Res Cardiol. 2015; 110(6):54.

55. Mendoza S A, Fang J, Gutterman D D, Wilcox D A, Bubolz A H, Li R, Suzuki M, Zhang D X. TRPV4-mediated endothelial Ca2+ influx and vasodilation in response to shear stress. Am J Physiol Heart Circ Physiol. 2010; 298 (2):H466-76.

56. Zhang D X, Mendoza S A, Bubolz A H, Mizuno A, Ge Z D, Li R, Warltier D C, Suzuki M, Gutterman D D. Transient receptor potential vanilloid type 4-deficient mice exhibit impaired endothelium-dependent relaxation induced by acetylcholine in vitro and in vivo. Hypertension. 2009; 53(3):532-8.

57. Healy S, Khan P, Davie J R. Immediate early response genes and cell transformation. Pharmacol Ther. 2013; 137 (1):64-77.

58. Fukuchi M, Kanesaki K, Takasaki I, Tabuchi A, Tsuda M. Convergent effects of Ca(2+) and cAMP signals on the expression of immediate early genes in neurons. Biochem Biophys Res Commun. 2015; 466(3):572-7.

59. Kobrinsky E. Heterogeneity of Calcium Channel/cAMP-Dependent Transcriptional Activation. Curr Mol Pharmacol. 2015; 8(1):54-60. PubMed PMID: 25966705.

60. Yin J C, Wallach J S, Del Vecchio M, Wilder E L, Zhou H, Quinn W G, Tully T. Induction of a dominant negative CREB transgene specifically blocks long-term memory in Drosophila. Cell. 1994; 79(1):49-58. PubMed PMID: 7923376.

61. Xu R, Paul B D, Smith D R, Tyagi R, Rao F, Khan A B, Blech D J, Vandiver M S, Harraz M M, Guha P, Ahmed I, Sen N, Gallagher M, Snyder S H. Inositol polyphosphate multikinase is a transcriptional coactivator required for immediate early gene induction. Proc Natl Acad Sci USA. 2013; 110(40):16181-6.

62. Liedtke W, Friedman J M. Abnormal osmotic regulation in trpv4-/- mice. Proc Natl Acad Sci USA. 2003; 100(23):13698-703.

63. Rahaman S O, Grove L M, Paruchuri S, Southern B D, Abraham S, Niese K A, Scheraga R G, Ghosh S, Thodeti C K, Zhang D X, Moran M M, Schilling W P, Tschumperlin D J, Olman M A. TRPV4 mediates myofibroblast differentiation and pulmonary fibrosis in mice. J Clin Invest. 2014; 124(12):5225-38.

64. Morgan J I, Curran T. Calcium as a modulator of the immediate-early gene cascade in neurons. Cell Calcium. 1988; 9(5-6):303-11. PubMed PMID: 3147142.

65. Lindecke A, Korte M, Zagrebelsky M, Horejschi V, Elvers M, Widera D, Prullage M, Pfeiffer J, Kaltschmidt B, Kaltschmidt C. Long-term depression activates transcription of immediate early transcription factor genes: involvement of serum response factor/Elk-1. Eur J Neurosci. 2006; 24(2):555-63.

66. Kar P, Parekh A B. Distinct spatial Ca2+signatures selectively activate different NFAT transcription factor isoforms. Mol Cell. 2015; 58(2):232-43.

67. Zhao L, Sullivan M N, Chase M, Gonzales A L, Earley S. Calcineurin/nuclear factor of activated T cells-coupled vanilliod transient receptor potential channel 4 ca2+ sparklets stimulate airway smooth muscle cell proliferation. Am J Respir Cell Mol Biol. 2014; 50(6):1064-75.

68. Lesch A, Hui X, Lipp P, Thiel G. Transient receptor potential melastatin-3 (TRPM3)-induced activation of AP-1 requires Ca2+ ions and the transcription factors c-Jun, ATF2, and ternary complex factor. Mol Pharmacol. 2015; 87(4): 617-28.

69. Jeon K I, Jono H, Miller C L, Cai Y, Lim S, Liu X, Gao P, Abe J, Li J D, Yan C. Ca2+/calmodulin-stimulated PDE1 regulates the beta-catenin/TCF signaling through PP2A B56 gamma subunit in proliferating vascular smooth muscle cells. FEBS J. 2010; 277(24):5026-39.

70. Kim P G, Nakano H, Das P P, Chen M J, Rowe R G, Chou S S, Ross S J, Sakamoto K M, Zon L I, Schlaeger T M, Orkin S H, Nakano A, Daley G Q. Flow-induced protein kinase A-CREB pathway acts via BMP signaling to promote HSC emergence. J Exp Med. 2015; 212(5):633-48.

71. Li J, Hou B, Tumova S, Muraki K, Bruns A, Ludlow M J, Sedo A, Hyman A J, McKeown L, Young R S, Yuldasheva N Y, Majeed Y, Wilson L A, Rode B, Bailey M A, Kim H R, Fu Z, Carter D A, Bilton J, Imrie H, Ajuh P, Dear T N, Cubbon R M, Kearney M T, Prasad K R, Evans P C, Ainscough J F, Beech D J. Piezo1 integration of vascular architecture with physiological force. Nature. 2014; 515 (7526):279-82.

72. Cahalan S M, Lukacs V, Ranade S S, Chien S, Bandell M, Patapoutian A. Piezo1 links mechanical forces to red blood cell volume. Elife. 2015; 4.

73. Glogowska E, Gallagher P G. Disorders of erythrocyte volume homeostasis. Int J Lab Hematol. 2015; 37 Suppl 1:85-91.

74. Archer N M, Shmukler B E, Andolfo I, Vandorpe D H, Gnanasambandam R, Higgins J M, Rivera A, Fleming M D, Sachs F, Gottlieb P A, Iolascon A, Brugnara C, Alper S L, Nathan D G. Hereditary xerocytosis revisited. Am J Hematol. 2014; 89(12):1142-6.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a population of hematopoietic stem cells (HSC), the method comprising:
providing a cell population ex vivo comprising hemogenic endothelial (HE) cells differentiated from human induced pluripotent stem cells (iPSCs) and provided on a flexible cell culture surface, and
subjecting the HE cells to cyclic 2-dimensional stretching by applying cyclic 2-dimensional stretching to the flexible cell culture surface having the HE cells thereon,
for a time and under conditions sufficient to stimulate endothelial-to-HSC transition.

2. The method of claim 1, wherein the HE cells are differentiated from iPSCs prepared from cells of a subject who is an autologous or allogeneic donor.

3. The method of claim 2, wherein the subject does not have a hematological malignancy.

* * * * *